(12) United States Patent
Germain et al.

(10) Patent No.: US 11,883,053 B2
(45) Date of Patent: Jan. 30, 2024

(54) ARTHROSCOPIC DEVICES AND METHODS

(71) Applicant: RELIGN Corporation, Campbell, CA (US)

(72) Inventors: Aaron Germain, San Jose, CA (US); Jacob Tonkel, San Jose, CA (US); Jan Echeverry, San Jose, CA (US)

(73) Assignee: Relign Corporation, Campbell, CA (US)

( * ) Notice: Subject to any disclaimer, the term of this patent is extended or adjusted under 35 U.S.C. 154(b) by 279 days.

(21) Appl. No.: 16/390,311

(22) Filed: Apr. 22, 2019

(65) Prior Publication Data

US 2019/0321063 A1    Oct. 24, 2019

Related U.S. Application Data

(60) Provisional application No. 62/661,551, filed on Apr. 23, 2018.

(51) Int. Cl.
*A61B 17/32* (2006.01)
*A61B 1/317* (2006.01)
(Continued)

(52) U.S. Cl.
CPC ........ *A61B 17/32002* (2013.01); *A61B 1/317* (2013.01); *A61B 18/1206* (2013.01);
(Continued)

(58) Field of Classification Search
CPC . A61B 17/32002; A61B 1/317; A61B 18/148; A61B 18/1206;
(Continued)

(56) References Cited

U.S. PATENT DOCUMENTS 7,150,747 B1    12/2006  McDonald et al.
7,674,263 B2 *   3/2010  Ryan .................... A61B 18/148
                                                          606/50
(Continued)

FOREIGN PATENT DOCUMENTS

GB         2552682 A      2/2018
WO    WO-2019209749 A1   10/2019

OTHER PUBLICATIONS

Allen-Bradley. AC Braking Basics. Rockwell Automation. Feb. 2001. 4 pages. URL: http://literature.rockwellautomation.com/idc/groups/literature/documents/wp/drives-wp004_-en-p.pdf.
(Continued)

*Primary Examiner* — Daniel W Fowler
*Assistant Examiner* — Lindsay Regan Lancaster
(74) *Attorney, Agent, or Firm* — SCHWEGMAN LUNDBERG & WOESSNER, P.A.

(57) ABSTRACT

An arthroscopic cutting probe includes an outer sleeve having a longitudinal bore and an outer cutting window at its distal end. The outer sleeve has a metal body electrically insulated over its exterior except for a portion at least partially surrounding the outer cutting window which comprises an active electrode. An inner sleeve is rotationally disposed in a bore of the outer sleeve, and the inner sleeve has a distal end, a proximal end and a longitudinal passageway having an electrically conductive inner surface which comprises a return electrode. A dielectric cutting member is attached to the distal end of the inner sleeve and has a central passage extending from an inner cutting window at its distal end to an opening at its proximal end. The opening at the proximal end is contiguous with the longitudinal passageway in the inner sleeve, and rotation of the inner sleeve relative to the outer sleeve causes the inner cutting window to rotate past the outer cutting window to resect tissue
(Continued)

received through the cutting windows as they pass each other.

19 Claims, 18 Drawing Sheets

(51) Int. Cl.
  *A61B 18/14*  (2006.01)
  *A61B 8/12*  (2006.01)
  *A61B 18/12*  (2006.01)
  *A61B 18/00*  (2006.01)

(52) U.S. Cl.
  CPC .. *A61B 18/148* (2013.01); *A61B 2018/00577* (2013.01); *A61B 2018/00589* (2013.01); *A61B 2018/00595* (2013.01); *A61B 2018/00601* (2013.01); *A61B 2018/126* (2013.01); *A61B 2018/1213* (2013.01)

(58) Field of Classification Search
  CPC .......... A61B 2018/00601; A61B 2018/00577; A61B 2018/00595; A61B 2018/1213; A61B 2018/126; A61B 2018/00589; A61B 18/1445; A61B 2018/00196; A61B 2090/067; A61B 2018/1422; A61B 90/98; A61B 2017/00876; A61B 2017/00398; A61B 2017/0046; A61B 2017/320024; A61B 2017/320028; A61B 2017/320004; A61B 2018/00208; A61B 2218/007
  See application file for complete search history.

(56) References Cited

U.S. PATENT DOCUMENTS

| | | | |
|---|---|---|---|
| 8,221,404 B2 | 7/2012 | Truckai | |
| 8,323,280 B2 | 12/2012 | Germain et al. | |
| 9,089,344 B2 * | 7/2015 | Rubin | A61B 17/32 |
| 9,204,918 B2 | 12/2015 | Germain et al. | |
| 9,247,983 B2 | 2/2016 | Truckai et al. | |
| 9,277,954 B2 | 3/2016 | Germain et al. | |
| 9,585,675 B1 | 3/2017 | Germain et al. | |
| 9,592,085 B2 | 3/2017 | Germain et al. | |
| 9,603,656 B1 | 3/2017 | Germain et al. | |
| 9,681,913 B2 | 6/2017 | Orczy-Timko et al. | |
| 9,795,434 B2 | 10/2017 | Germain et al. | |
| 9,855,675 B1 | 1/2018 | Germain et al. | |
| 10,004,556 B2 | 6/2018 | Orczy-Timko et al. | |
| 10,022,140 B2 | 7/2018 | Germain et al. | |
| 10,028,767 B2 | 7/2018 | Germain et al. | |
| 10,052,149 B2 | 8/2018 | Germain et al. | |
| 10,595,889 B2 | 3/2020 | Germain et al. | |
| 2002/0038122 A1 * | 3/2002 | Peters | A61B 18/1485 606/45 |
| 2007/0016099 A1 * | 1/2007 | Chin | A61B 10/0275 600/564 |
| 2008/0188848 A1 * | 8/2008 | Deutmeyer | A61B 18/1485 606/40 |
| 2012/0330292 A1 * | 12/2012 | Shadduck | A61B 18/00 606/29 |
| 2014/0336643 A1 * | 11/2014 | Orczy-Timko | A61B 18/149 606/45 |
| 2015/0173827 A1 | 6/2015 | Bloom et al. | |
| 2015/0265337 A1 * | 9/2015 | Bloom | A61B 18/1485 606/48 |
| 2016/0113706 A1 | 4/2016 | Truckai et al. | |
| 2016/0157916 A1 | 6/2016 | Germain et al. | |
| 2016/0346036 A1 * | 12/2016 | Orczy-Timko | A61B 18/14 |
| 2017/0128083 A1 | 5/2017 | Germain et al. | |
| 2017/0172648 A1 | 6/2017 | Germain et al. | |
| 2017/0252099 A1 | 9/2017 | Orczy-Timko et al. | |
| 2017/0258512 A1 | 9/2017 | Germain et al. | |
| 2017/0258519 A1 | 9/2017 | Germain et al. | |
| 2017/0290602 A1 | 10/2017 | Germain et al. | |
| 2017/0303990 A1 | 10/2017 | Benamou et al. | |
| 2018/0000534 A1 | 1/2018 | Germain et al. | |
| 2018/0008334 A1 | 1/2018 | Germain et al. | |
| 2018/0093391 A1 | 4/2018 | Germain et al. | |
| 2018/0161088 A1 | 6/2018 | Poser et al. | |
| 2018/0263649 A1 | 9/2018 | Germain et al. | |
| 2018/0303509 A1 | 10/2018 | Germain et al. | |
| 2018/0317957 A1 | 11/2018 | Germain et al. | |
| 2019/0008538 A1 | 1/2019 | Germain et al. | |
| 2019/0008541 A1 | 1/2019 | Norton et al. | |
| 2019/0015151 A1 | 1/2019 | Germain et al. | |
| 2019/0021788 A1 | 1/2019 | Germain et al. | |
| 2019/0059983 A1 | 2/2019 | Germain et al. | |
| 2019/0083121 A1 | 3/2019 | Benamou et al. | |

OTHER PUBLICATIONS

Allen-Bradley. What Is Regeneration? Braking / Regeneration Manual: Regeneration Overview. Revision 1.0. Rockwell Automation. Accessed Apr. 24, 2017. 6 pages. URL: https://www.ab.com/support/abdrives/documentation/techpapers/RegenOverview01.pdf.

International search report with written opinion dated Aug. 16, 2019 for PCT/US2019/028581.

"International Application Serial No. PCT/US2019/028581, International Preliminary Report on Patentability dated Nov. 5, 2020", 8 pgs.

* cited by examiner

ARTHROSCOPIC DEVICES AND METHODS

CROSS-REFERENCE TO RELATED APPLICATION

The present application claims the benefit of provisional application No. 62/661,551, filed on Apr. 23, 2018, the full disclosure of which is incorporated herein by reference.

BACKGROUND OF THE INVENTION

1. Field of the Invention

This invention relates to a medical system that includes variations of motor-driven tubular cutter or arthroscopic shavers that are configured for both mechanical cutting and electrosurgical cutting, ablation and coagulation procedures.

In endoscopic and other surgical procedures including subacromial decompression, anterior cruciate ligament reconstruction involving notchplasty, and arthroscopic resection of the acromioclavicular joint, there is a need for cutting and removal of bone and soft tissue. Currently, surgeons use arthroscopic shavers and burrs having rotational cutting surfaces to remove hard tissue in such procedures.

To promote efficiency, some endoscopic tool systems include reusable hand piece and a selection of interchangeable tool probes having different working ends. Such working ends may each have two or more functionalities, such as soft tissue removal and hard tissue resection, so such tools systems can provide dozens of specific functionalities, providing great flexibility.

It is therefore an object of the present invention to provide additional interchangeable and other tool probes and methods for their use, such as improved arthroscopic tissue cutting probes and removal system wherein a motor-driven electrosurgical device is provided for selectively cutting and removing bone or soft tissue from a joint or other site. It is a further object of the present invention to provide a single arthroscopic cutting probe or other handheld device that is capable of both mechanical and electrosurgically enhanced cutting of both soft and hard tissues. At least some of these objectives will be met by the inventions described herein.

2. Description of the Background Art

Patents of interest include U.S. Pat. No. 7,150,747. Related, commonly owned patents and published applications include: U.S. Pat. Nos. 8,221,404; 8,323,280; 9,204,918; 9,277,954; 9,247,983; 9,592,085; 9,585,675; 9,603,656; 9,681,913; 9,855,675; 10,028,767; 10,052,149; 9,795,434; and 10,022,140; and U.S. Pat. Publication Nos. US 2016-0113706; US 2016-0157916; US 2017-0128083; US 2017-0172648; US 2017-0258519; US 2017-0258512; US 2017-0290602; US 2017-0303990; US 2017-0252099; US 2018-0000534; US 2018-0161088; US 2018-0008334; US 2018-0093391; US 2019-0015151; US 2018-0263649; US 2019-0083121; US 2019-0008538; US 2018-0303509; US 2018-0317957; US 2019-0021788; US 2019-0059983; and US 2019-0008541, the full disclosures of which are incorporated herein by reference.

SUMMARY OF THE INVENTION

The present invention provides improved apparatus and methods for resecting tissue in arthroscopic and other surgical procedures. In particular, the present invention provides a single tool, typically in the form of an arthroscopic cutting probe, which can resect tissue both mechanically and with electrosurgical enhancement. The tool preferably employs a dual sleeve rotating tubular cutter, wherein the inner sleeve rotates I the outer sleeve with each sleeve typically having a cutting window formed at or near a distal end thereof. At least the outer cutting window will have an active electrode disposed partially or fully around its periphery, typically being an exposed portion of a metal wall of the tubular cutter. A return electrode will typically be provided along at least a portion of an interior surface of a debris extraction lumen in the inner tubular cutter (bipolar design), although in other instances it may be provided separately from the cutting probe or other tool, typically in the form of a grounding pad placed externally on the patient's body, typically on the lower back (monopolar design).

In a first aspect of the present invention, an arthroscopic cutting probe comprises an outer sleeve, an inner sleeve, and a dielectric cutting member typically attached to a distal end of the inner sleeve. The outer sleeve will typically be a tubular member having a longitudinal bore and an outer cutting window formed at a distal end thereof, typically being cut or otherwise formed through a distal region of the tubular wall. The tubular body of the outer sleeve typically comprises a metal which is electrically insulated over at least a portion of its exterior except for a specific portion that at least partially surrounds the outer cutting window. The exposed region of the body which at least partially surrounds the outer cutting window will typically act as an active electrode when the cutting probe is used in an electrosurgical cutting mode.

The inner sleeve of the arthroscopic cutting probe may be rotationally disposed in a bore or other central passageway of the outer sleeve, thus being disposed coaxially about a longitudinal axis. The inner sleeve will have a distal end, a proximal end, and a longitudinal passageway extending between the ends. The longitudinal passageway will typically have an electrically conductive inner surface extending at least partially along its length and which can act as a return electrode in at least some bipolar embodiments. Optionally, the electrically conductive inner surface may be formed by a metal tubular member that forms the inner sleeve. Alternatively, the inner conductive member could be a layer, sleeve, or other separate element formed along the interior surface of an otherwise electrically non-conductive inner sleeve member.

The dielectric cutting member of the arthroscopic cutting probe will usually be attached directly to a distal end of the inner sleeve and will typically have a central passage extending from an inner cutting window at its distal end to an opening at its proximal end. The opening at the proximal end will typically be contiguous with the longitudinal passageway in the inner sleeve. Thus, the inner cutting window can act as a port or inlet for receiving cutting debris and other materials resulting from the tissue resection and the longitudinal passageway of the inner sleeve will allow the debris to be removed, typically by applying a negative pressure at a proximal end of the longitudinal passageway. as described further below. The negative pressure will allow draw tissue into the openeing formed by the cutting windows as the come into alignment to enable and enhance resection of the tissue in both the mechanical and electrosurgical cutting modes. By rotating the inner sleeve relative to the outer sleeve, the inner cutting member is caused to rotate past the outer cutting window to resect tissue received through the cutting windows as they pass each other.

In specific aspects of the arthroscopic cutting probes of the present invention, the longitudinal passageway of the inner sleeve will be configured to be coupled to a negative pressure source. By applying a negative pressure to the longitudinal passageway, the tissue debris may be drawn through the inner cutting window and central passage of the dielectric cutting member and then be extracted through the longitudinal passageway to be removed from the body.

In various specific aspects of the arthroscopic cutting probes of the present invention, the dielectric cutting member may comprise a wear-resistant ceramic material, such as yttria-stabilized zirconia, magnesia-stabilized zirconia, ceria-stabilized zirconia, zirconia toughened alumina, silicon nitride, and the like.

In other specific instances, the arthroscopic cutting probes of the present invention may have bullet-shaped distal ends with the outer cutting window formed by cutting a portion of the distal end to leave an opening or aperture which forms the outer cutting window. Typically, the dielectric cutting member will also have a bullet-shaped distal end with the inner cutting window formed thereacross.

In specific embodiments, the inner cutting member will be configured to nest in the outer cutting window when the two cutting windows are in alignment.

In other specific instances, the active electrode of the outer sleeve may comprise a metal edge exposed when forming the cutting window in a wall of the inner sleeve.

In still other specific instances, the dielectric cutting member will have an aperture disposed in a wall at a location opposite to that of the outer cutting window.

In still other specific instances, the inner cutting window will have an area equal to at least 50% of an area of the outer cutting window. In yet further instances, the aperture in the dielectric cutting member will have an area equal to less than 25% of the area of the outer cutting window.

In a second aspect of the present invention, an arthroscopic cutting system comprises an arthroscopic cutting probe, generally as described above. The arthroscopic cutting system further comprises at least a motor drive unit and a radiofrequency (RF) power supply. The motor drive unit is configured to be coupled to the inner sleeve of the arthroscopic cutting probe in a manner to rotate the inner sleeve relative to the outer sleeve. In this way, the inner and outer cutting members can be caused to rotate past one another to resect tissue which is received in the cutting windows when they pass in and out of alignment. The RF power supply is configured to be coupled to the active electrode and the return electrode, and the controller is configured to control the motor drive unit and the RF power supply.

Thus, the controller that can be used to operate the arthroscopic cutting system in at least two modes of operation. First, the motor drive unit can be operated to rotate the inner sleeves within the outer sleeve while the RF power supply is de-energized so that no current is delivered to the electrodes. In a second operating mode, the controller causes the motor drive unit to rotate the inner sleeve within the outer sleeve and further causes the RF power supply to deliver energy to the active electrode and return electrode so that the tissue resection is electrosurgically enhanced.

In specific embodiments, the arthroscopic cutting system may further comprise a negative pressure source configured to be coupled to the longitudinal passageway of the inner sleeve. In this way, a negative pressure can be applied to a proximal end of the longitudinal passageway to draw tissue through the cutting windows as they pass by each other. The negative pressure will further draw cutting debris which enters the distal end of the longitudinal passageway toward the proximal end where it can be collected in a conventional collection receptacle.

In a third aspect of the present invention, a method for resecting tissue comprises providing an arthroscopic cutting probe as generally described above. The dielectric cutting member on the cutting probe is engaged against a target tissue, and the inner cutting window is rotated past the outer cutting window to resect tissue received through the cutting windows as they pass by each other while the dielectric cutting member remains engaged with the tissue.

In specific instances of the methods herein, the cutting windows can be operated without applying RF current so that cutting is principally mechanical. In other aspects, RF current will be applied to the active and return electrodes to allow for electrosurgically enhanced cutting. The methods will often further comprise applying negative pressure to the longitudinal passageway of the inner sleeve during either mechanical or electrosurgical resection modes. The negative pressure serves to both draw the tissue initially through the windows as they are passing by one another and further to draw tissue debris down the longitudinal passageway after the tissue has been resected. The resection methods of the present invention are suitable for both cutting hard tissue and soft tissue, typically with RF enhancement used in cutting hard tissues, such as bone.

BRIEF DESCRIPTION OF THE DRAWINGS

Various embodiments of the present invention will now be discussed with reference to the appended drawings. It should be appreciated that the drawings depict only typical embodiments of the invention and are therefore not to be considered limiting in scope.

DETAILED DESCRIPTION OF THE INVENTION

The present invention relates to bone cutting and tissue removal devices and related methods of use. Several variations of the invention will now be described to provide an overall understanding of the principles of the form, function and methods of use of the devices disclosed herein. In general, the present disclosure provides for variations of arthroscopic tools adapted for cutting bone, soft tissue, meniscal tissue, and for RF ablation and coagulation. The arthroscopic tools are typically disposable and are configured for detachable coupling to a non-disposable hand piece that carries a motor drive component. This description of the general principles of this invention is not meant to limit the inventive concepts in the appended claims.

Figure 1:
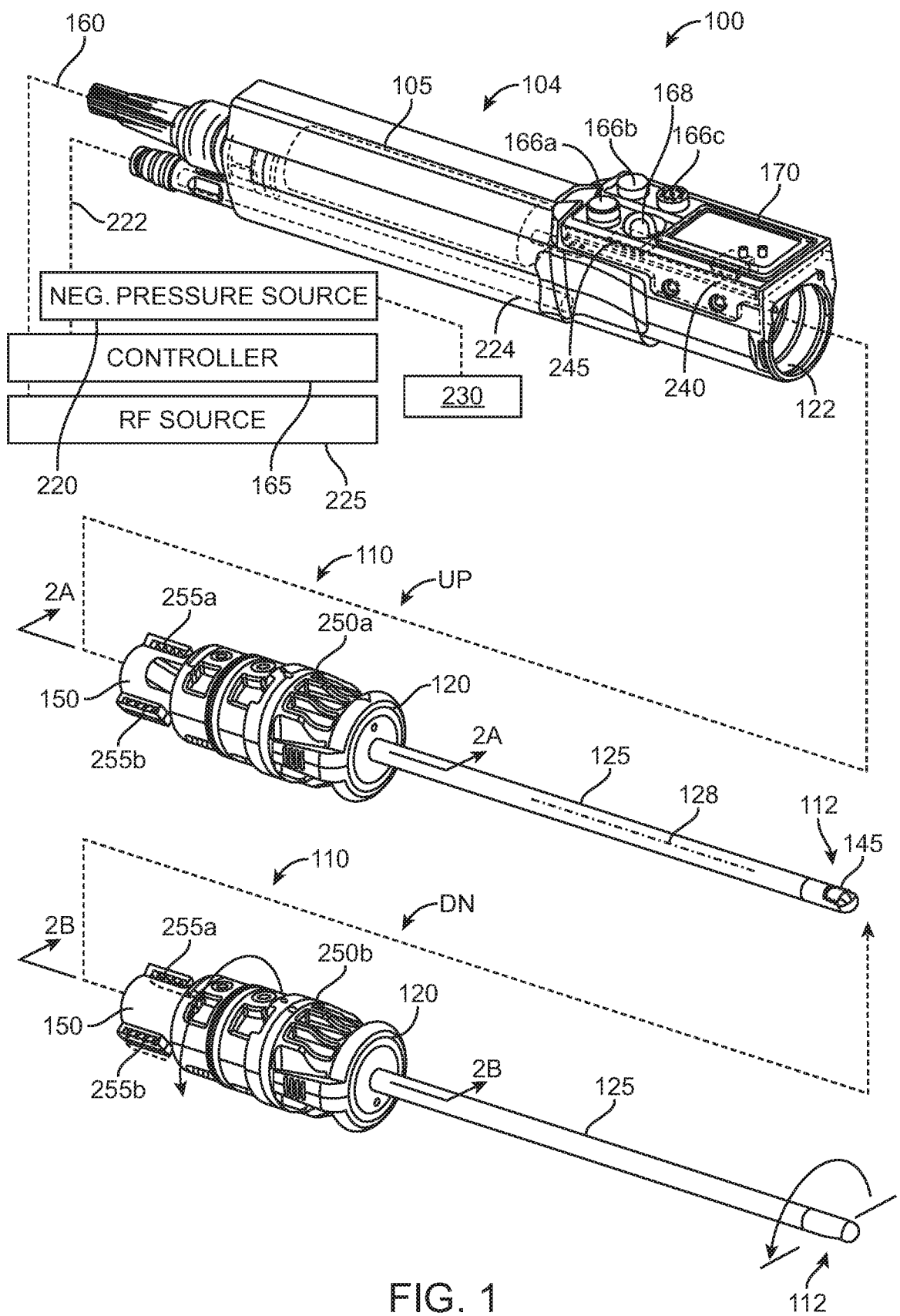
FIG. 1 is a perspective view of an arthroscopic cutting system that includes reusable hand piece with a motor drive and a detachable single-use cutting probe, wherein the cutting probe is shown in two orientations as it may be coupled to the hand piece with the probe and working end in upward orientation or a downward orientation relative to the hand piece, and wherein the hand piece includes an LCD screen for displaying operating parameters of system during use together with control actuators on the hand piece.

In one variation shown in FIG. 1, the arthroscopic system 100 of the present invention provides a hand piece 104 with motor drive 105 and a disposable shaver assembly or probe 110 with a proximal hub 120 that can be received by receiver or bore 122 in the hand piece 104. In one aspect, the probe 110 has a working end 112 that carries a high-speed rotating cutter that is configured for use in many arthroscopic surgical applications, including but not limited to treating bone in shoulders, knees, hips, wrists, ankles and the spine.

Figure 2A:
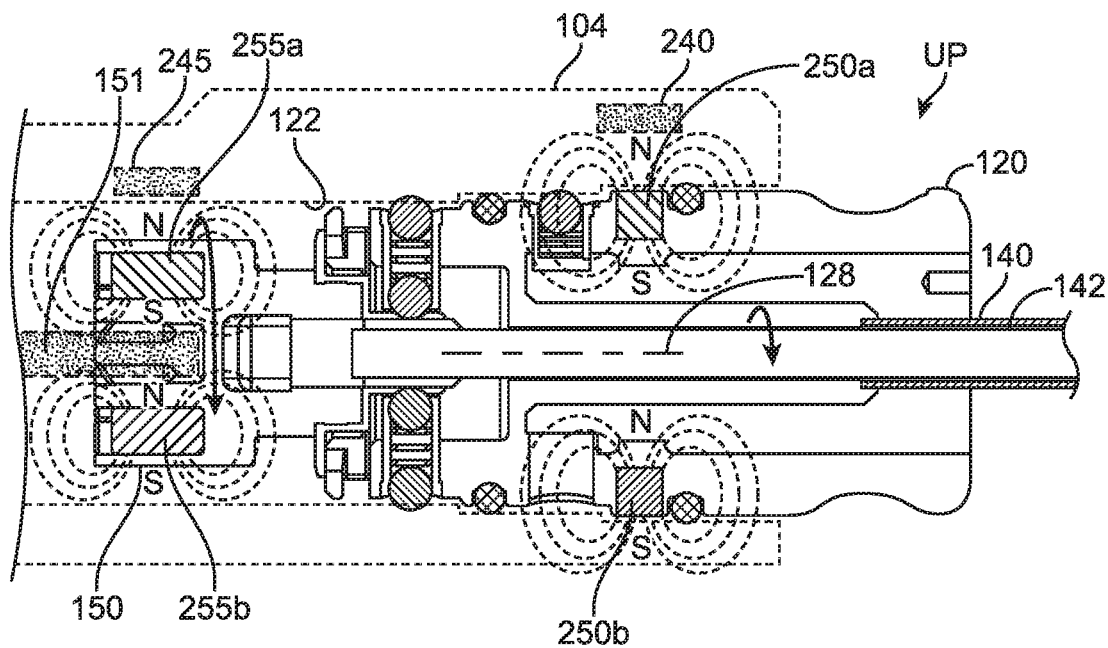
FIG. 2A is an enlarged longitudinal sectional view of the hub of the probe of FIG. 1 taken along line 2A-2A of FIG. 1 with the hub and probe in an upward orientation relative to the hand piece, further showing Hall effect sensors carried by the hand piece and a plurality of magnets carried by the probe hub for device identification, for probe orientation and determining the position of motor driven components of the probe relative to the hand piece.
Figure 3A:
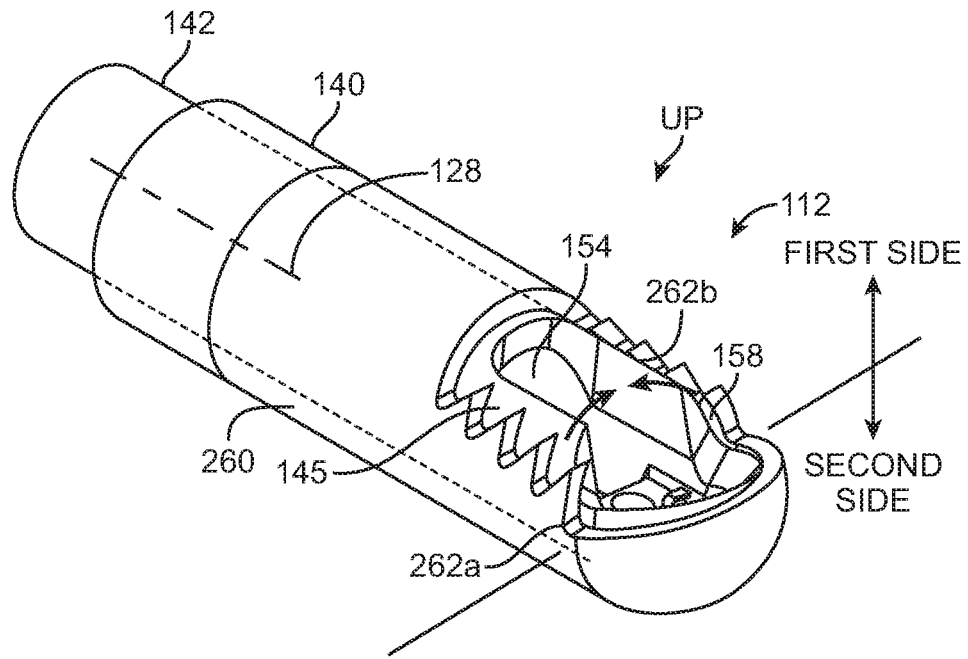
FIG. 3A is an enlarged perspective view of the working end of the probe of FIG. 1 in an upward orientation with the rotatable cutting member in a first position relative to the outer sleeve wherein the window in the cutting member is aligned with the window of the outer sleeve.
Figure 3B:
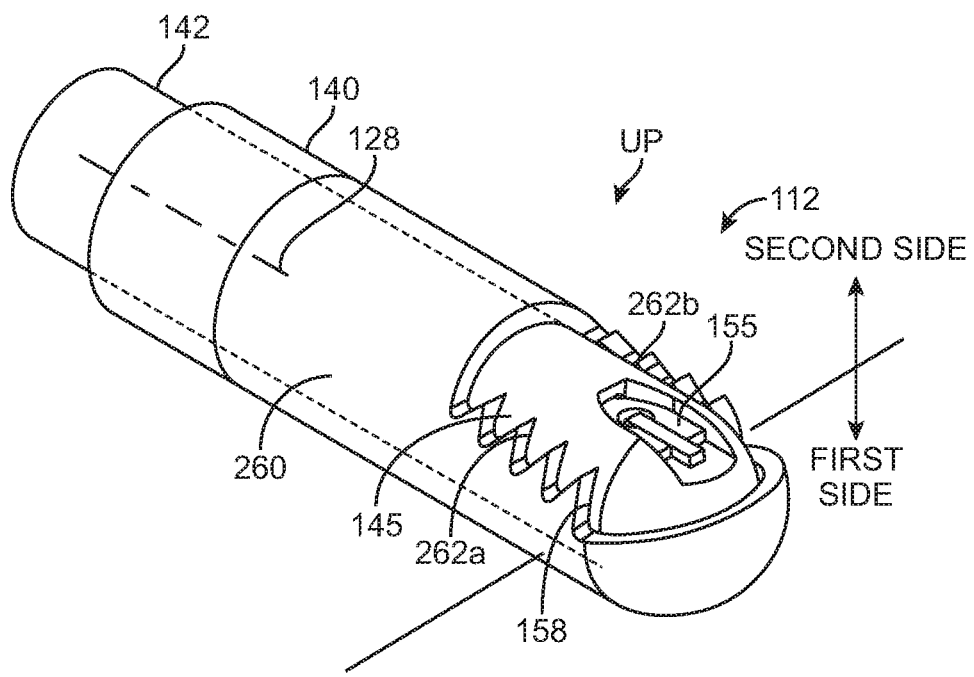
FIG. 3B is a perspective view of the working end of FIG. 1 in an upward orientation with the rotatable cutting member in a second position relative to the outer sleeve wherein the electrode carried by the cutting member is aligned with a centerline of the window of the outer sleeve.

In FIGS. 1, 2A and 3A, it can be seen that probe 110 has a shaft 125 extending along longitudinal axis 128 that comprises an outer sleeve 140 and an inner sleeve 142 rotatably disposed therein with the inner sleeve 142 carrying a distal ceramic cutting member 145 (FIG. 3A). The shaft 125 extends from the proximal hub 120 wherein the outer sleeve 140 is coupled in a fixed manner to the hub 120 which can be an injection molded plastic, for example, with the outer sleeve 140 insert molded therein. The inner sleeve 142 is coupled drive coupling 150 that is configured for coupling to the rotating motor shaft 151 of motor drive unit 105. More in particular, the rotatable cutting member 145 that is fabricated of a ceramic material with sharp cutting edges on opposing sides 152a and 152b of window 154 therein for cutting soft tissue. The motor drive 105 is operatively coupled to the ceramic cutter to rotate the cutting member at speeds ranging from 1,000 rpm to 20,000 rpm. In FIG. 3B, it can be seen that cutting member 145 also carries an RF electrode 155 in a surface opposing the window 154. The cutting member 145 rotates and shears tissue in the toothed opening or window 158 in the outer sleeve 140 (FIG. 3A). A probe of the type shown in FIG. 1 is described in more detail in co-pending and commonly owned patent application Ser. No. 15/421,264 filed Jan. 31, 2017 (Atty. Docket 41879-714.201) titled ARTHROSCOPIC DEVICES AND METHODS which is incorporated herein in its entirety by this reference.

As can be seen in FIG. 1, the probe 110 is shown in two orientations for detachable coupling to the hand piece 104. More particularly, the hub 120 can be coupled to the hand piece 104 in an upward orientation indicated at UP and a downward orientation indicated at DN where the orientations are 180° opposed from one another. It can be understood that the upward and downward orientations are necessary to orient the working end 112 either upward or downward relative to the hand piece 104 to allow the physician to interface the cutting member 145 with targeted tissue in all directions without having to manipulate the hand piece in 360° to access tissue.

In FIG. 1, it can be seen that the handle 104 is operatively coupled by electrical cable 160 to a controller 165 which controls the motor drive unit 105 Actuator buttons 166*a*, 166*b* or 166*c* on the handle 104 can be used to select operating modes, such as various rotational modes for the ceramic cutting member 145. In one variation, a joystick 168 can be moved forward and backward to adjust the rotational speed of the ceramic cutting member 145. The rotational speed of the cutter can continuously adjustable, or can be adjusted in increments up to 20,000 rpm. An LCD screen 170 is provided in the hand piece for displaying operating parameters, such as cutting member RPM, mode of operation, etc.

Figure 4:
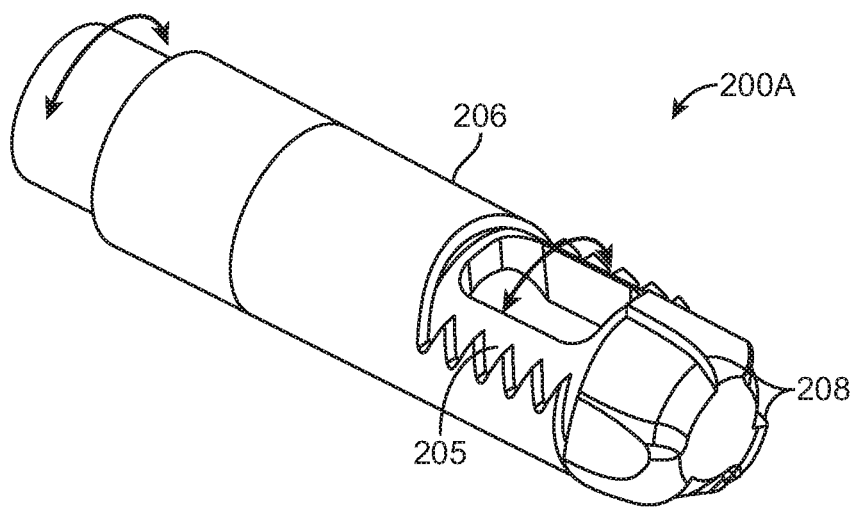
FIG. 4 is a perspective view of a working end of a variation of a probe that may be detachably coupled to the hand piece of FIG. 1, wherein the working end includes a bone burr extending distally from the outer sleeve.
Figure 5:
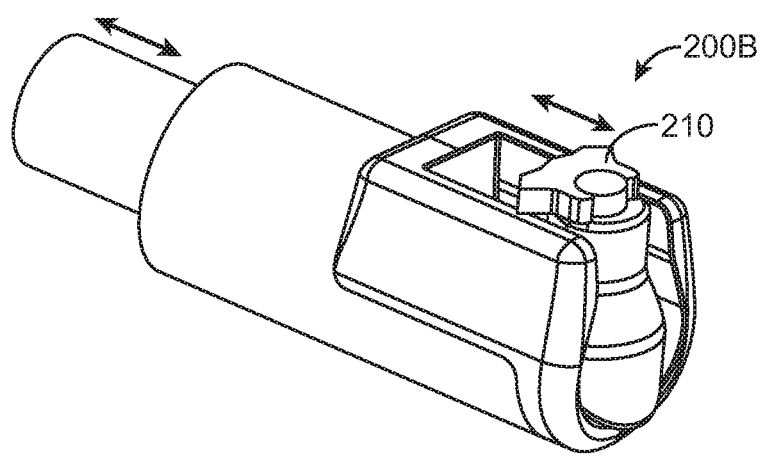
FIG. 5 is a perspective view of a working end of a variation of a probe that may be detachably coupled to the hand piece of FIG. 1, wherein the working end has a reciprocating electrode.
Figure 6:
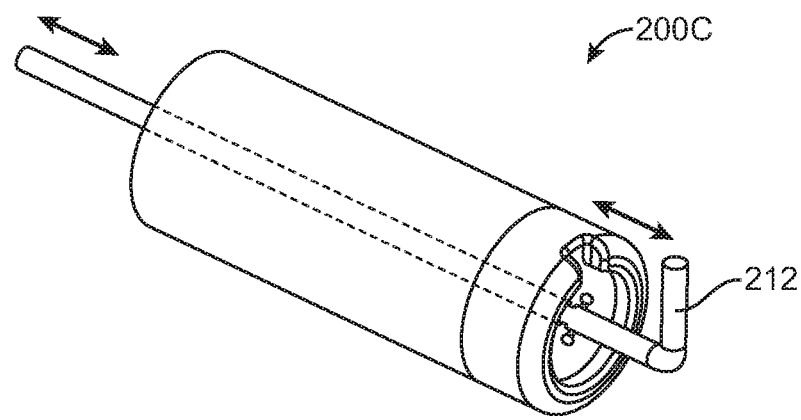
FIG. 6 is a perspective view of a working end of another variation of a probe that may be detachably coupled to the hand piece of FIG. 1, wherein the working end has a hook electrode that has extended and non-extended positions.
Figure 7:
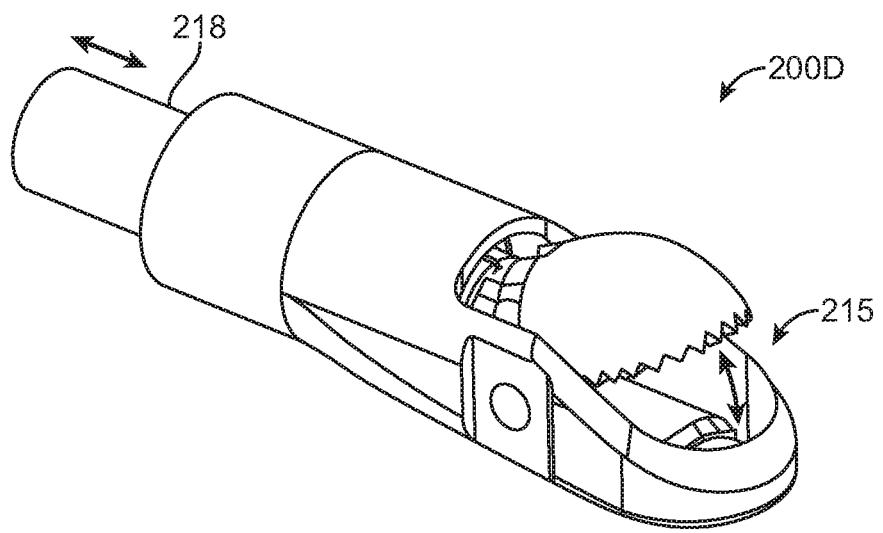
FIG. 7 is a perspective view of a working end of yet another variation of a probe that may be detachably coupled to the hand piece of FIG. 1, wherein the working end has an openable-closeable jaw structure for cutting tissue.

It can be understood from FIG. 1 that the system 100 and hand piece 104 is adapted for use with various disposable probes which can be designed for various different functions and procedures For example, FIG. 4 illustrates a different variation of a probe working end 200A that is similar to working end 112 of probe 110 of FIGS. 3A-3B, except the ceramic cutting member 205 extends distally from the outer sleeve 206 and the cutting member has burr edges 208 for cutting bone. The probe of FIG. 4 is described in more detail in co-pending and commonly owned patent application Ser. No. 15/271,184 filed Sep. 20, 2016 titled ARTHROSCOPIC DEVICES AND METHODS. FIG. 5 illustrates a different variation of a probe working end 200B with a reciprocating electrode 210 in a type of probe described in more detail in co-pending and commonly owned patent application Ser. No. 15/410,723 filed Jan. 19, 2017 titled ARTHROSCOPIC DEVICES AND METHODS. In another example, FIG. 6 illustrates another variation of a probe working end 200C that has an extendable-retractable hook electrode 212 in a probe type described in more detail in co-pending and commonly owned patent application Ser. No. 15/454,342 filed Mar. 9, 2017 titled ARTHROSCOPIC DEVICES AND METHODS. In yet another example, FIG. 7 illustrates a variation of a working end 200D in a probe type having an openable-closable jaw structure 215 actuated by reciprocating member 218 for trimming meniscal tissue or other tissue as described in more detail in co-pending and commonly owned patent application Ser. No. 15/483,940 filed Apr. 10, 2017 titled ARTHROSCOPIC DEVICES AND METHODS. All of the probes of FIGS. 4-7 can have a hub similar to hub 120 of probe 110 of FIG. 1 for coupling to the same hand piece 104 of FIG. 1, with some of the probes (see FIGS. 5-7) having a hub mechanism for converting rotational motion to linear motion. All of the patent applications just identified in this paragraph are incorporated herein by this reference.

FIG. 1 further shows that the system 100 also includes a negative pressure source 220 coupled to aspiration tubing 222 which communicates with a flow channel 224 in hand piece 104 and can cooperate with any of the probes 110, 200A, 200B or 200C of FIGS. 1-3B, 4, 5 and 6. In FIG. 1 it also can be seen that the system 100 includes an RF source 225 which can be connected to an electrode arrangement in any of the probes 110, 200A, 200B or 200C of FIGS. 1-3B, 4, 5 and 6. The controller 165 and microprocessor therein together with control algorithms are provided to operate and control all functionality, which includes controlling the motor drive 105 to move a motor-driven component of any probe working end 110, 200A, 200B or 200C, as well as for controlling the RF source 225 and the negative pressure source 220 which can aspirate fluid and tissue debris to collection reservoir 230.

As can be understood from the above description of the system 100 and hand piece 104, the controller 165 and controller algorithms need to be configured to perform and automate many tasks to provide for system functionality. In a first aspect, controller algorithms are needed for device identification so that when any of the different probes types 110, 200A, 200B, 200C or 200D of FIGS. 1 and 4-7 are coupled to hand piece 104, the controller 165 will recognize the probe type and then select algorithms for operating the motor drive 105, RF source 225 and negative pressure source 220 as is needed for the particular probe. In a second aspect, the controller is configured with algorithms that identify whether the probe is coupled to the hand piece 104 in an upward or downward orientation relative to the hand piece, wherein each orientation requires a different subset of the operating algorithms. In another aspect, the controller has separate control algorithms for each probe type wherein some probes have a rotatable cutter while others have a reciprocating electrode or jaw structure. In another aspect, most if not all the probes 110, 200A, 200B, 200C and 200D (FIGS. 1, 4-7) require a default "stop" position in which the motor-driven component is stopped in a particular orientation within the working end. For example, a rotatable cutter 145 with an electrode 155 needs to have the electrode centered within an outer sleeve window 158 in a default position such as depicted in FIG. 3B. Some of these systems, algorithms and methods of use are described next.

Figure 2B:
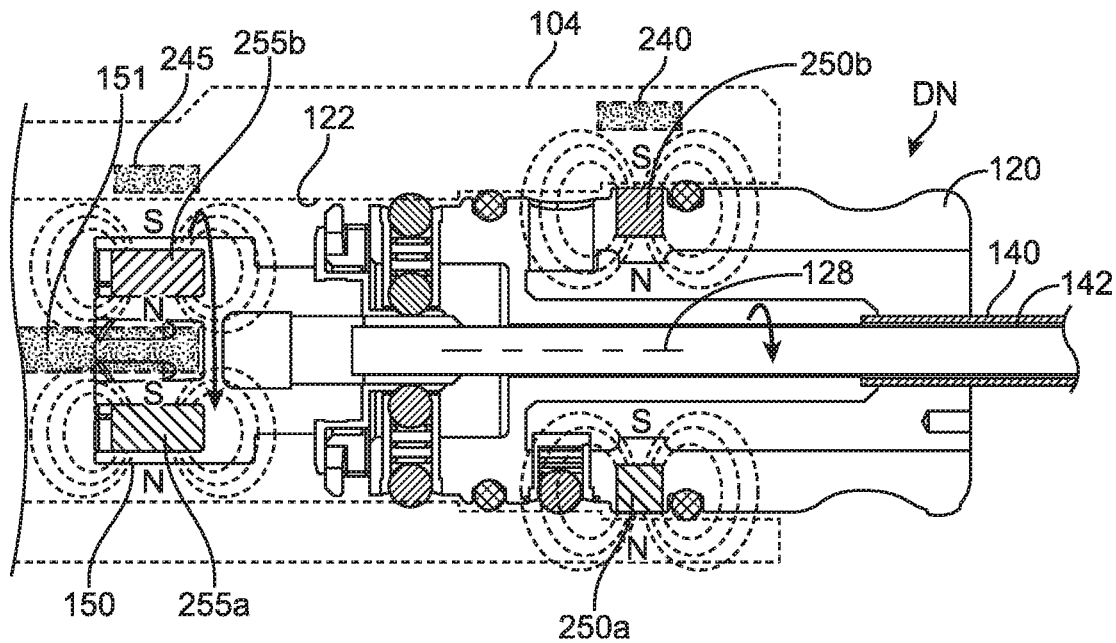
FIG. 2B is a sectional view of the hub of FIG. 1 taken along line 2B-2B of FIG. 1 with the hub and probe in a downward orientation relative to the hand piece showing the Hall effect sensor and magnets having a different orientation compared to that of FIG. 2A.

Referring to FIGS. 1 and 2A-2B, it can be seen that hand piece 104 carries a first Hall effect sensor 240 in a distal region of the hand piece 104 adjacent the receiving passageway 122 that receives the hub 120 of probe 110. FIG. 2A corresponds to the probe 110 and working end 112 in FIG. 1 being in the upward orientation indicated at UP. FIG. 2B corresponds to probe 110 and working end 112 in FIG. 1 being in the downward orientation indicated at DN. The hand piece 104 carries a second Hall effect sensor 245 adjacent the rotatable drive coupling 150 of the probe 110. The probe 110 carries a plurality of magnets as will be described below that interact with the Hall effect sensors 240, 245 to provide multiple control functions in cooperation with controller algorithms, including (i) identification of the type of probe coupled to the hand piece, (ii) the upward or downward orientation of the probe hub 120 relative to the hand piece 104, and (iii) the rotational position and speed of rotating drive collar 150 from which a position of either rotating or reciprocating motor-driven components can be determined.

The sectional views of FIGS. 2A-2B show that hub 120 of probe 110 carries first and second magnets 250*a* and 250*b* in a surface portion thereof. The Hall sensor 240 in hand piece 104 is in axial alignment with either magnet 250*a* or 250*b* when the probe hub 120 is coupled to hand piece 104 in an upward orientation (FIGS. 1 and 2A) or a downward orientation (FIGS. 1 and 2B). In one aspect as outlined above, the combination of the magnets 250*a* and 250*b* and the Hall sensor 240 can be used to identify the probe type. For example, a product portfolio may have from 2 to 10 or more types of probes, such as depicted in FIGS. 1 and 4-7, and each such probe type can carry magnets 250*a*, 250*b* having a specific, different magnetic field strength. Then, the Hall sensor 240 and controller algorithms can be adapted to read the magnetic field strength of the particular magnet(s) in the probe which can be compared to a library of field strengths that correspond to particular probe types. Then, a Hall identification signal can be generated or otherwise provided to the controller 165 to select the controller algorithms for operating the identified probe, which can include parameters for operating the motor drive 105, negative pressure source 220 and/or RF source 225 as may be required for the probe type. As can be seen in FIGS. 1, 2A and 2B, the probe hub 120 can be coupled to hand piece 104 in upward and downward orientations, in which the North (N) and South (S) poles of the magnets 250a, 250b are reversed relative to the probe axis 128. Therefore, the Hall sensor 240 and associated algorithms look for magnetic field strength regardless of polarity to identify the probe type.

Referring now to FIGS. 1, 2A-2B and 3A-3B, the first and second magnets 250a and 250b with their different orientations of North (N) and South (S) poles relative to central longitudinal axis 128 of hub 120 are also used to identify the upward orientation UP or the downward orientation DN of hub 120 and working end 112. In use, as described above, the physician may couple the probe 110 to the hand piece receiving passageway 122 with the working end 112 facing upward or downward based on his or her preference and the targeted tissue. It can be understood that controller algorithms adapted to stop rotation of the cutting member 145 in the window 158 of the outer sleeve 104 of working end 112 need to "learn" whether the working end is facing upward or downward, because the orientation or the rotating cutting member 145 relative to the hand piece and Hall sensor 240 would vary by 180°. The Hall sensor 240 together with a controller algorithm can determine the orientation UP or the downward orientation DN by sensing whether the North (N) or South (S) pole of either magnet 250a or 250b is facing upwardly and is proximate the Hall sensor 240.

In another aspect of the invention, in probe 110 (FIG. 1) and other probes, the motor-driven component of a working end, such as rotating cutter 145 of working end 112 of FIGS. 1 and 3A-3B needs to stopped in a selected rotational position relative to a cut-out opening or window 158 in the outer sleeve 140. Other probe types may have a reciprocating member or a jaw structure as described above, which also needs a controller algorithm to stop movement of a moving component in a selected position, such as the axial-moving electrodes of FIGS. 5-6 and the jaw structure of FIG. 7. In all probes, the motor drive 105 couples to the rotating drive coupling 150, thus sensing the rotational position of the drive coupling 150 can be used to determine the orientation of the motor-driven component in the working end. More in particular, referring to FIGS. 1 and 2A-2B, the drive coupling 150 carries third and fourth magnets 255a or 255b with the North (N) and South (S) poles of magnets 255a or 255b being reversed relative to the probe axis 128. Thus, Hall sensor 245 can sense when each magnet rotates passes the Hall sensor and thereby determine the exact rotational position of the drive coupling 150 twice on each rotation thereof (once for each magnet 255a, 255b). Thereafter, a controller tachometer algorithm using a clock can determine and optionally display the RPM of the drive coupling 150 and, for example, the cutting member 145 of FIG. 3A.

In another aspect of the invention, the Hall sensor 245 and magnets 255a and 255b (FIGS. 1 and 2A) are used in a set of controller algorithms to stop the rotation of a motor-driven component of a working end, for example, cutting member 145 of FIGS. 1 and 3A-3B in a pre-selected rotational position. In FIG. 3A, it can be seen that the inner sleeve 142 and a "first side" of cutting member 145 and window 154 therein is stopped and positioned in the center of window 158 of outer sleeve 140. The stationary position of cutting member 145 and window 154 in FIG. 3A may be used for irrigation or flushing of a working space to allow for maximum fluid outflow through the probe.

FIG. 3B depicts inner sleeve 142 and a "second side" of cutting member 145 positioned about the centerline of window 158 in the outer sleeve 140. The stationary or stopped position of cutting member 145 in FIG. 3B is needed for using the RF electrode 155 to ablate or coagulate tissue. It is important that the electrode 155 is maintained along the centerline of the outer sleeve window 158 since the outer sleeve 140 typically comprises return electrode 260. The position of electrode 155 in FIG. 3B is termed herein a "centerline default position". If the cutting member 145 and electrode 155 were rotated so as to be close to an edge 262a or 262b of window 158 in outer sleeve 140, RF current could arc between the electrodes 155 and 260 and potentially cause a short circuit disabling the probe. Therefore, a robust and reliable stop mechanism is required which is described next.

As can be understood from FIGS. 1 and 2A-2B, the controller 165 can always determine in real time the rotational position of drive coupling 150 and therefore the angular or rotational position of the ceramic cutting member 145 and electrode 155 can be determined. A controller algorithm can further calculate the rotational angle of the electrode 155 away from the centerline default position as the Hall sensor 245 can sense lessening of magnetic field strength as a magnet 255a or 255b in the drive coupling 150 rotates the electrode 155 away from the centerline default position. Each magnet has a specified, known strength and the algorithm can use a look-up table with that lists fields strengths corresponding to degrees of rotation away from the default position. Thus, if the Hall signal responsive to the rotated position of magnet 255a or 255b drops a specified amount from a known peak value in the centerline default position, it means the electrode 155 has moved away from the center of the window 158. In one variation, if the electrode 155 moves a selected rotational angle away from the centerline position during RF energy delivery to the electrode, the algorithm turns off RF current instantly and alerts the physician by an aural and/or visual signal, such as an alert on the LCD screen 170 on hand piece 104 and/or on a screen on a controller console (not shown). The termination of RF current delivery thus prevents the potential of an electrical arc between electrode 155 and the outer sleeve electrode 260.

It can be understood that during use, when the electrode 155 is in the position shown in FIG. 3B, the physician may be moving the energized electrode over tissue to ablate or coagulate tissue. During such use, the cutting member 145 and electrode 155 can engage or catch on tissue which inadvertently rotate the electrode 155 out of the default centerline position. Therefore, the system provides a controller algorithm, herein called an "active electrode monitoring" algorithm, wherein the controller continuously monitors position signals generated by Hall sensor 245 during RF energy delivery in both an ablation mode and a coagulation mode to determine if the electrode 155 and inner sleeve 142 have been bumped off the centerline position. In a variation, the controller algorithms can be configured to then re-activate the motor drive 105 to move the inner sleeve 142 and electrode 155 back to the default centerline position sleeve if electrode 155 had been bumped off the centerline position. In another variation, the controller algorithms can be configured to again automatically deliver RF current to RF electrode 155 when it is moved back to the to the default centerline position. Alternatively, the controller 165 can require the physician to manually re-start the delivery of RF current to the RF electrode 155 when it is moved back to the to the centerline position. In an aspect of the invention, the drive coupling 150 and thus magnets 255a and 255b are attached to inner sleeve 142 and cutting member 145 in a pre-determined angular relationship relative to longitudinal axis 128 so that the Hall sensor generates signals responsive to magnets 255a, 255b is the same for all probes within a probe type to thus allow the controller algorithm to function properly.

Figure 8:
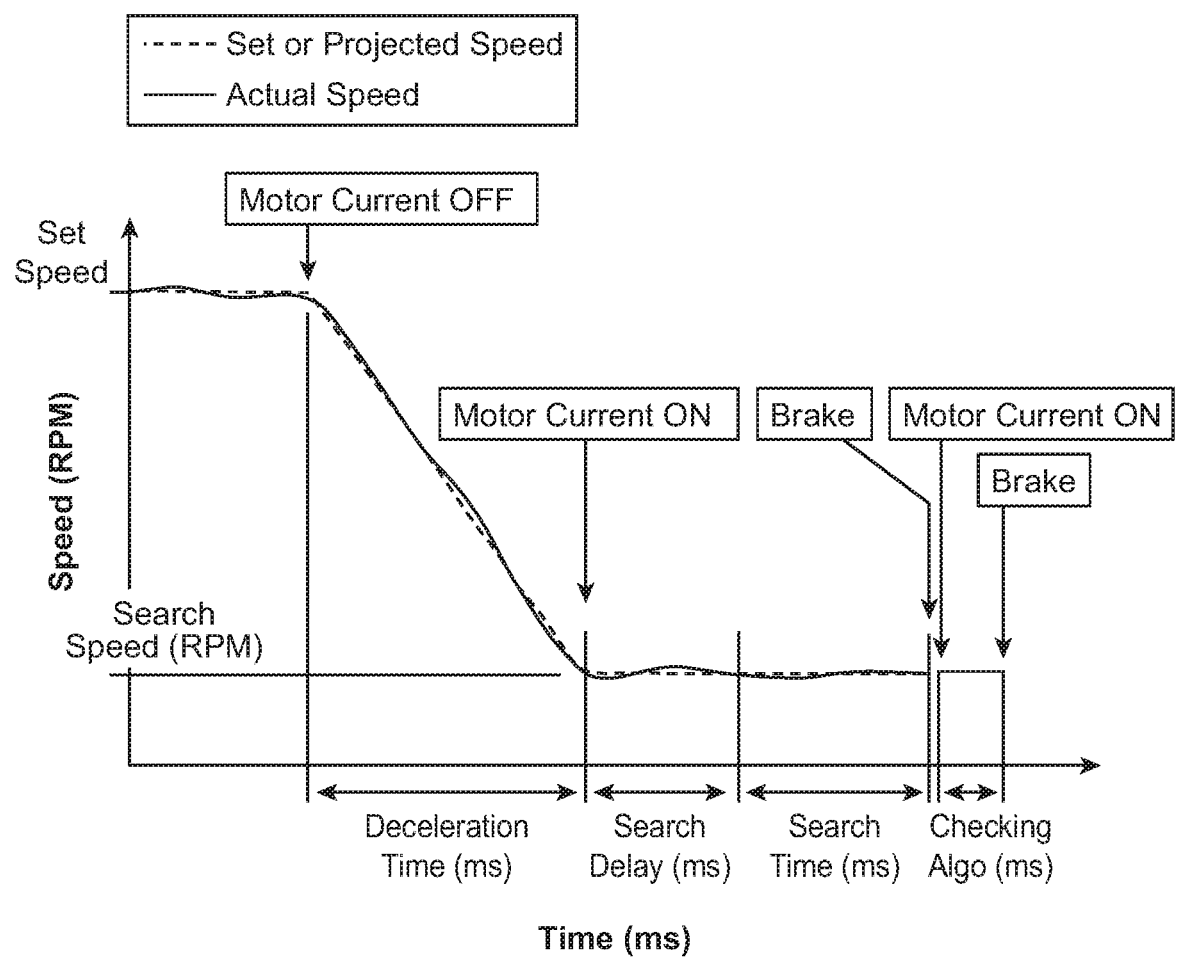
FIG. 8 is a chart relating to set speeds for a probe with a rotating cutting member as in FIGS. 1 and 3A that schematically shows the method used by a controller algorithm for stopping rotation of the cutting member in a selected default position.

Now turning to the stop mechanism or algorithms for stopping movement of a motor-driven component of working end 112, FIG. 8 schematically illustrates the algorithm and steps of the stop mechanism. In one variation, referring to FIG. 8, the stop mechanism corresponding to the invention uses (i) a dynamic braking method and algorithm to stop the rotation of the inner sleeve 142 and cutting member 145 (FIGS. 1, 3A-3B) in an initial position, and thereafter (ii) a secondary checking algorithm is used to check the initial stop position that was attained with the dynamic braking algorithm, and if necessary, the stop algorithm can re-activate the motor drive 105 to slightly reverse (or move forward) the rotation of drive coupling 150 and inner sleeve 142 as needed to position the cutting member 145 and electrode 155 within at the centerline position or within 0° to 5° of the targeted centerline default position. Dynamic braking is described further below. FIG. 8 schematically illustrates various aspects of controller algorithms for controlling the rotational speed of the cutting member and for stopping the cutting member 145 in the default centerline position.

In FIG. 8, it can be understood that the controller 165 is operating the probe 110 of FIGS. 1 and 3A-3B at a "set speed" which may be a PID controlled, continuous rotation mode in one direction or may be an oscillating mode where the motor drive 105 rotates the cutting member 145 in one direction and then reverses rotation as is known in the art. At higher rotational speeds such as 1,000 RPM to 20,000 RPM, it is not practical or feasible to acquire a signal from Hall sensor 245 that indicates the position of a magnet 255a or 255b in the drive coupling 150 to apply a stop algorithm. In FIG. 8, when the physician stop cutting with probe 110 by releasing actuation of an actuator button or foot pedal, current to the motor drive 105 is turned off. Thereafter, the controller algorithm uses the Hall sensor 245 to monitor deceleration of rotation of the drive coupling 150 and inner sleeve 142 until a slower RPM is reached. The deceleration period may be from 10 ms to 1 sec and typically is about 100 ms. When a suitable slower RPM is reached which is called a "search speed" herein (see FIG. 8), the controller 165 re-activates the motor drive 105 to rotate the drive coupling at a low speed ranging from 10 RPM to 1,000 RPM and in one variation is between 50 RPM and 250 RPM. An initial "search delay" period ranging from 50 ms to 500 ms is provided to allow the PID controller to stabilize the RPM at the selected search speed. Thereafter, the controller algorithm monitors the Hall position signal of magnet strength and when the magnet parameter reaches a predetermined threshold, for example, when the rotational position of drive coupling 150 and electrode 155 correspond to the centerline default position of FIG. 3B, the control algorithm then applies dynamic braking to instantly stop rotation of the motor drive shaft 151, drive coupling 150 and the motor-driven component of the probe. FIG. 8 further illustrates that the controller can check the magnet/drive coupling 150 position after the braking and stopping steps. If the Hall position signal indicates that the motor-driven component is out of the targeted default position, the motor drive 105 can be re-activated to move the motor-driven component and thereafter the brake can be applied again as described above.

Dynamic braking as shown schematically in FIG. 8 may typically stop the rotation of the drive coupling 150 with a variance of up to about 0°-15° of the targeted stop position, but this can vary even further when different types of tissue are being cut and impeding rotation of the cutting member 145, and also depending on whether the physician has completely disengaged the cutting member from the tissue interface when the motor drive is de-activated. Therefore, dynamic braking alone may not assure that the default or stop position is within a desired variance.

As background, the concept of dynamic braking is described in the following literature: https://www.ab.com/support/abdrives/documentation/techpapers/RegenOverview01.pdf and http://literature.rockwellautomation.com/idc/groups/literature/documents/wp/drives-wp004_-en-p.pdf. Basically, a dynamic braking system provides a chopper transistor on the DC bus of the AC PWM drive that feeds a power resistor that transforms the regenerative electrical energy into heat energy. The heat energy is dissipated into the local environment. This process is generally called dynamic braking with the chopper transistor and related control and components called the chopper module and the power resistor called the dynamic brake resistor. The entire assembly of chopper module with dynamic brake resistor is sometimes referred to as the dynamic brake module. The dynamic brake resistor allows any magnetic energy stored in the parasitic inductance of that circuit to be safely dissipated during the turn off of the chopper transistor.

The method is called dynamic braking because the amount of braking torque that can be applied is dynamically changing as the load decelerates. In other words, the braking energy is a function of the kinetic energy in the spinning mass and as it declines, so does the braking capacity. So the faster it is spinning or the more inertia it has, the harder you can apply the brakes to it, but as it slows, you run into the law of diminishing returns and at some point, there is no longer any braking power left.

In another aspect of the invention, a method has been developed to increase the accuracy of the stopping mechanism which is a component of the positioning algorithm described above. It has been found that each magnet in a single-use probe may vary slightly from its specified strength. As described above, the positioning algorithm uses the Hall effect sensor 245 to continuously monitor the field strength of magnets 255a and 255b as the drive coupling 150 rotates and the algorithm determines the rotational position of the magnets and drive coupling based on the field strength, with the field strength rising and falling as a magnet rotates past the Hall sensor. Thus, it is important for the algorithm to have a library of fields strengths that accurately correspond to degrees of rotation away from a peak Hall signal when a magnet is adjacent the sensor 245. For this reason, an initial step of the positioning algorithm includes a "learning" step that allow the controller to learn the actual field strength of the magnets 255a and 255b which may vary from the specified strength. After a new single-use probe 110 (FIG. 1) is coupled to the hand piece 104, and after actuation of the motor drive 105, the positioning algorithm will rotate the drive coupling at least 180° and more often at least 360° while the Hall sensor 245 quantifies the field strength of the particular probe's magnets 255a and 255b. The positioning algorithm then stores the maximum and minimum Hall signals (corresponding to North and South poles) and calibrates the library of field strengths that correspond to various degrees of rotation away from a Hall min-max signal position when a magnet is adjacent the Hall sensor.

In general, a method of use relating to the learning algorithm comprises providing a hand piece with a motor drive, a controller, and a probe with a proximal hub configured for detachable coupling to the hand piece, wherein the motor drive is configured to couple to a rotating drive coupling in the hub and wherein the drive coupling carries first and second magnets with North and South poles positioned differently relative to said axis, and coupling the hub to the hand piece, activating the motor drive to thereby rotate the drive coupling and magnets at least 180°, using a hand piece sensor to sense the strength of each magnet, and using the sensed strength of the magnets for calibration in a positioning algorithm that is responsive to the sensor sensing the varying strength of the magnets in the rotating drive coupling to thereby increase accuracy in calculating the rotational position of the drive coupling 150.

Another aspect of the invention relates to an enhanced method of use using a probe working end with an electrode, such as the working end 112 of FIGS. 1 and 3B. As described above, a positioning algorithm is used to stop rotation of the electrode 155 in the default centerline position of FIG. 3B. An additional "slight oscillation" algorithm is used to activate the motor drive 105 contemporaneous with RF current to the electrode 155, particularly an RF cutting waveform for tissues ablation. The slight oscillation thus provides for a form of oscillating RF ablation. The slight oscillation algorithm rotates the electrode 155 in one direction to a predetermined degree of rotation, which the controller algorithms determine from the Hall position signals. Then, the algorithm reverses direction of the motor drive to rotate in the opposite direction until Hall position signals indicate that the predetermined degree of rotation was achieved in the opposite direction away from the electrode's default centerline position. The predetermined degree of angular motion can be any suitable rotation that is suitable for dimensions of the outer sleeve window, and in one variation is from 1° to 30° in each direction away from the centerline default position. More often, the predetermined degree of angular motion is from 5° to 15° in each direction away from the centerline default. The slight oscillation algorithm can use any suitable PID controlled motor shaft speed, and in one variation the motor shaft speed is from 50 RPM to 5,000 RPM, and more often from 100 RPM to 1,000 RPM. Stated another way, the frequency of oscillation can be from 20 Hz to 2,000 Hz and typically between 40 Hz and 400 Hz.

While the above description of the slight oscillation algorithm is provided with reference to electrode 155 on a rotating cutting member 145 of FIG. 3B, it should be appreciated that a reciprocating electrode 212 as shown in the working end 200C of FIG. 6 end could also be actuated with slight oscillation. In other words, the hook shape electrode 212 of FIG. 6 could be provided with a frequency of oscillation ranging from 20 Hz to 2,000 Hz and typically between 40 Hz and 400 Hz.

Figure 9A:
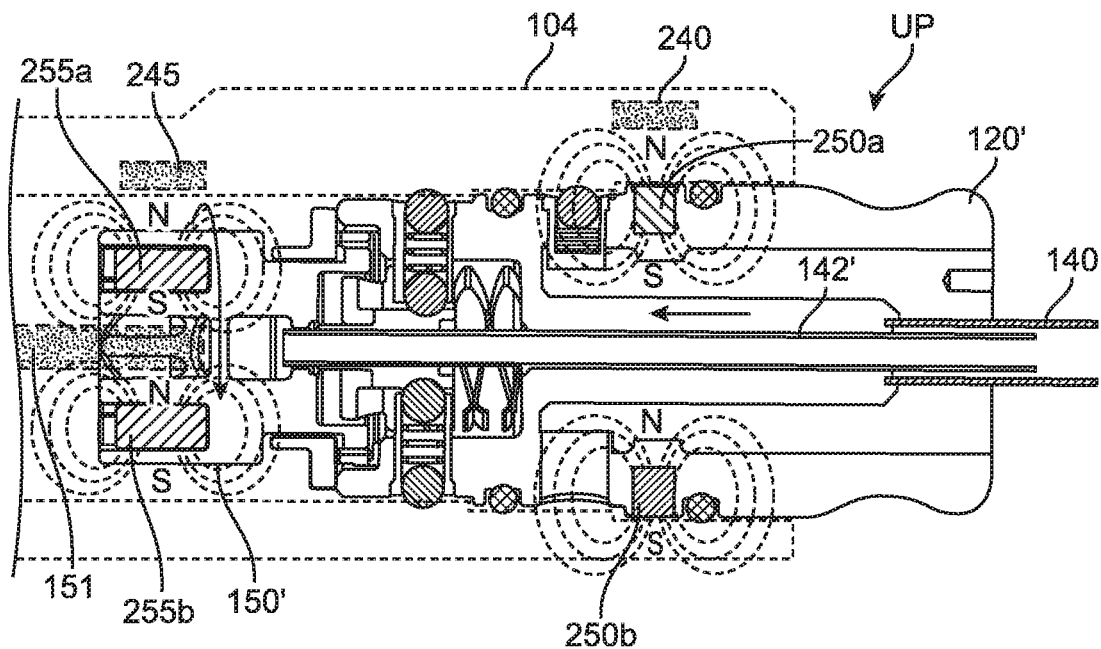
FIG. 9A is a longitudinal sectional view of a probe hub that is similar to that of FIG. 2A, except the hub of FIG. 9A has an internal cam mechanism for converting rotational motion to linear motion to axially reciprocate an electrode as in the working end of FIG. 5, wherein FIG. 9A illustrated the magnets in the hub and drive coupling are the same as in FIG. 2A and the hub is in an upward facing position relative to the hand piece.
Figure 9B:
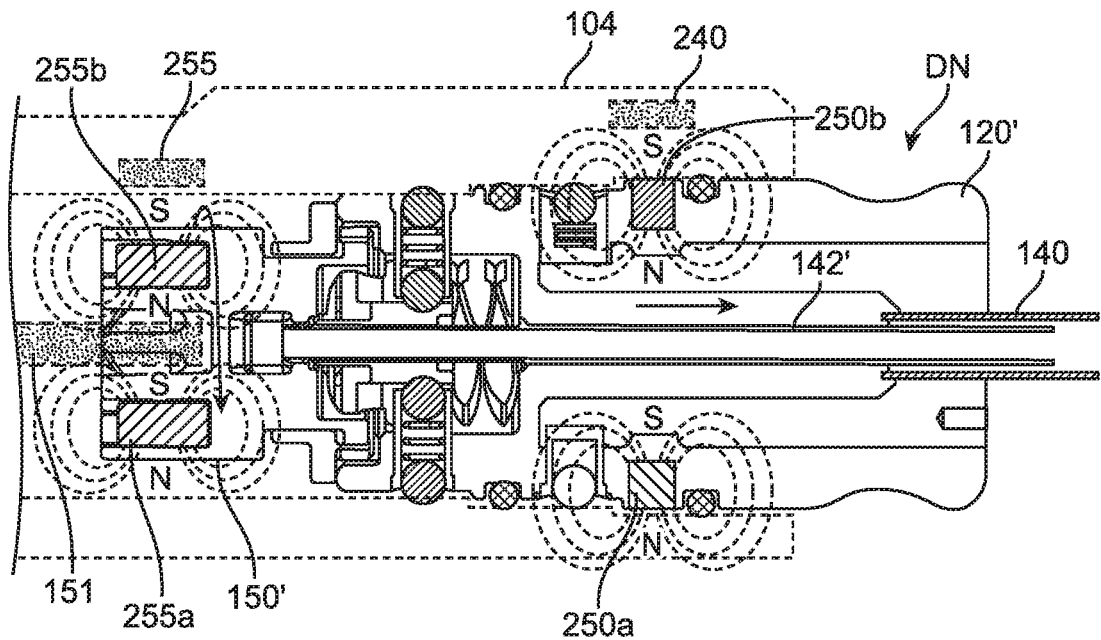
FIG. 9B is a sectional view of the hub of FIG. 9A rotated 180° in a downward facing position relative to the hand piece.

FIGS. 9A-9B are longitudinal sectional views of a probe hub 120' that corresponds to the working end 200B of FIG. 5 which has a reciprocating electrode 210. In FIGS. 9A-9B, the hand piece 104 and Hall affect sensors 240 and 245 are of course the same as described above as there is no change in the hand piece 104 for different types of probes. The probe hub 120' of FIGS. 9A-9B is very similar to the hub 120 of FIGS. 2A-2B with the first and second identification/orientation magnets 250a and 250b being the same. The third and fourth rotational position magnets 255a and 255b also are the same and are carried by drive coupling 150'. The probe hub 120' of FIGS. 9A-9B only differs in that the drive coupling 150 rotates with a cam mechanism operatively coupled to inner sleeve 142' to convert rotational motion to linear motion to reciprocate the electrode 210 in working end 200B of FIG. 5. A similar hub for converting rotational motion to linear motion is provided for the working ends 200C and 200D of FIGS. 6 and 7, respectively, which each have a reciprocating component (212, 218) in its working end.

Now turning to FIGS. 10 and 11A-11C, another variation of an arthroscopic shaver or resection probe 400 is shown which somewhat similar to that of FIGS. 1 and 3A-3B which comprises a tubular cutter having a proximal hub 402 coupled to an elongated shaft assembly 405. The shaft assembly comprises an outer sleeve 410 and a concentric inner sleeve 415 that extends along axis 418 to a working end 420. The hub 402 again is adapted for coupling to a hand piece and motor drive operated by a controller and controller algorithms having the features as described in previous embodiments for rotating the inner sleeve 415 as well as stopping the inner sleeve 415 in a selected rotational position, such as a window-closed or window-open position. The working end 420 again has an outer sleeve window 422 that cooperates with an inner sleeve window 425 for engaging and resecting tissue.

The variation in FIGS. 10 and 11A-11C, the shaft assembly 405 differs in that the outer sleeve 410 has a distal end portion that comprises a dielectric body or housing 440 in which the outer window 422 is disposed. In one variation, the proximal 426a and medial portions 426b of the outer sleeve 410 that extend from the hub 402 comprise a thin wall, electrically conductive metal tube 428, such as a stainless steel. As will be described further below, a proximal or medial portion of the metal tube functions as an electrode indicated at 430 in FIG. 10. In a typical variation, the dielectric housing 440 comprises a ceramic material, a glass material, a polymeric material or a combination thereof. In some variations, the dielectric housing 440 can be carried within a metal support portion 442 of the metal outer tube 428 which extends underneath or partly surrounding the dielectric housing 440.

Figure 11A:
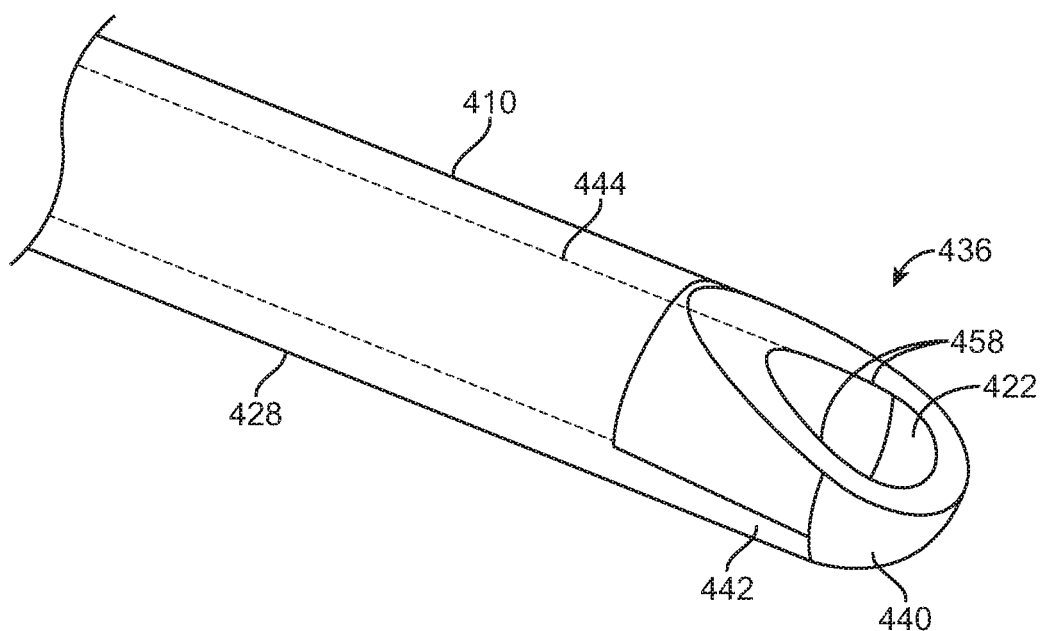
FIG. 11A is perspective view of the working end of the outer sleeve of the probe of FIG. 10 separated from the inner sleeve.

FIG. 11A shows the working end 436 of the outer sleeve 410 with outer window 422 separated from the inner sleeve 415. It can be seen that passageway or bore 444 extends through the outer sleeve 410 and the dielectric housing 440 in which the concentric inner sleeve 415 is rotationally disposed.

Figure 11B:
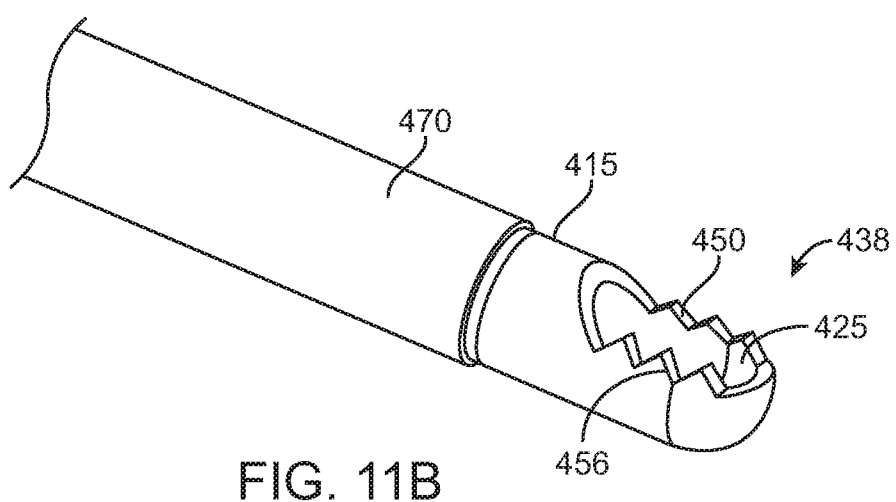
FIG. 11B is perspective view of the working end of the inner sleeve of the probe of FIG. 10 with the inner sleeve window facing upward.
Figure 11C:
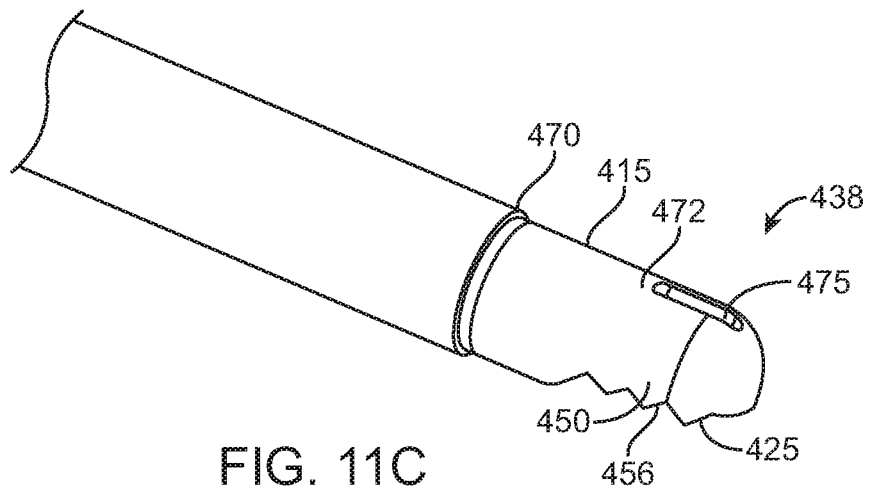
FIG. 11C is perspective view of the working end of the inner sleeve of FIG. 11B with the inner sleeve window facing downward.

FIG. 11B shows the working end 438 of the inner sleeve 415 separated from the outer sleeve 410 of FIG. 11A in a first position in which the inner sleeve window 425 is facing upwardly. FIG. 11C illustrates the same inner sleeve 415 rotated 180° so that the inner sleeve window 425 is facing downward. As can be seen in FIGS. 11B-11C, the inner sleeve 415 comprises a thin wall metal tube of a conductive material, such as stainless steel, which then can function as an electrode indicated at 450. Thus, the working end 438 of the inner sleeve 415 which carries the inner window 425 comprises electrode 450 which is configured with a close rotational fit in the bore 444 of the dielectric housing 440 so that the inner window edges 456, with optional teeth, and the edges 458 outer sleeve window and act like scissors for shearing or resecting tissue, either mechanically or electrosurgically, as will be described further below. Still referring to FIGS. 11A and 11B, the inner sleeve 415 is a thin layer 470 of an insulating polymer such as a heat shrink tubing or the parylene coating to electrically insulate the outer surface of inner sleeve 415 from the inner surface of the metal outer sleeve 428.

Figure 10:
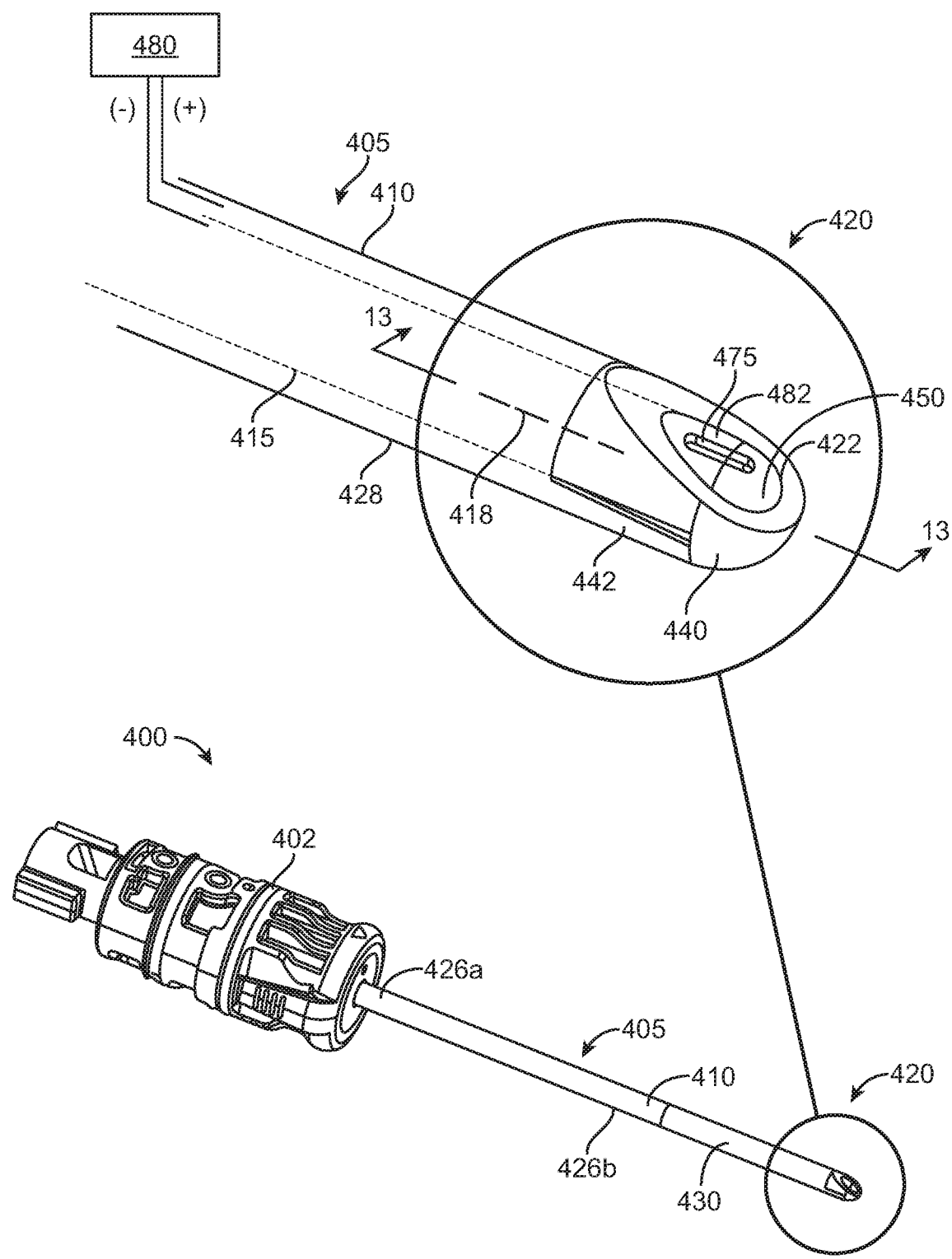
FIG. 10 is a perspective view of another variation of a probe that shows a motor-driven, rotating inner cutting sleeve that comprises an electrode and outer sleeve carrying a distal dielectric housing.

In another aspect of the invention as can be seen in FIGS. 10 and 11C, the back side 472 of the inner sleeve 415 opposing the inner sleeve window 425 has at least one opening 475 that is provided for fluid outflows therethrough when the inner sleeve 415 is rotated relative to the outer sleeve 410 to a window-closed position (see FIG. 1).

Figure 12:
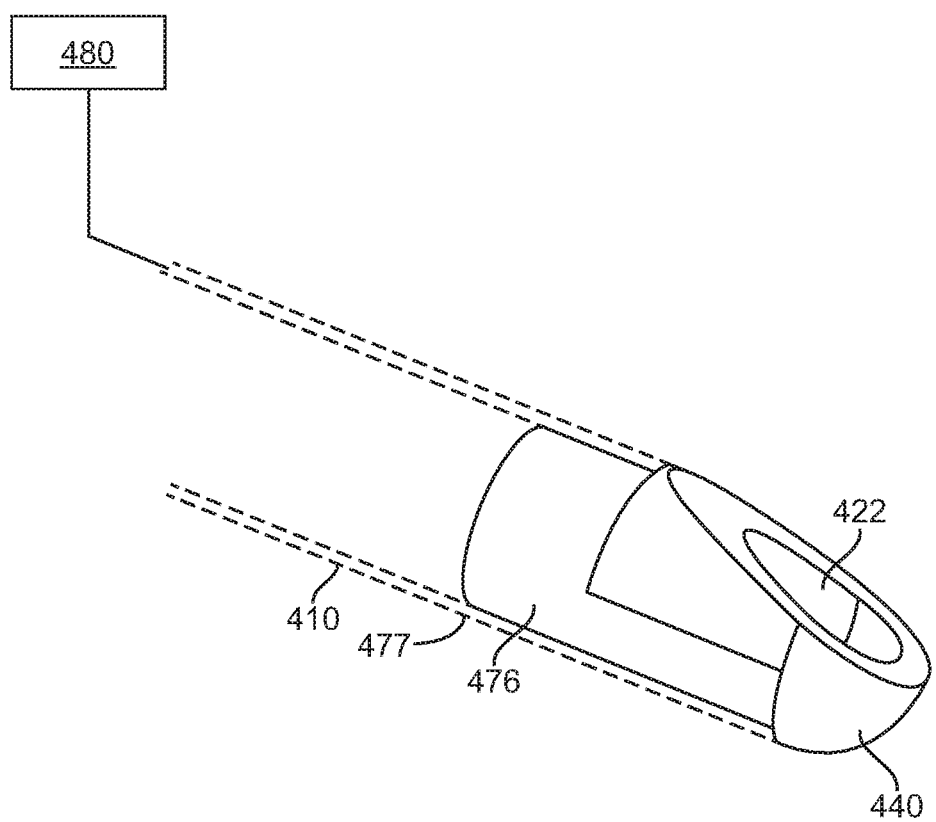
FIG. 12 is perspective view of the dielectric housing of FIG. 11A.

FIG. 12 illustrates the dielectric or ceramic housing 440 with the outer sleeve 415 in phantom view. It can be seen that the dielectric housing 440 has a recessed portion 476 in which the distal end 477 of outer sleeve 410 surrounds and supports the dielectric housing 440. The thickness of the wall of the dielectric housing around the window 422 can range from about 0.05" to 0.20".

Figure 13:
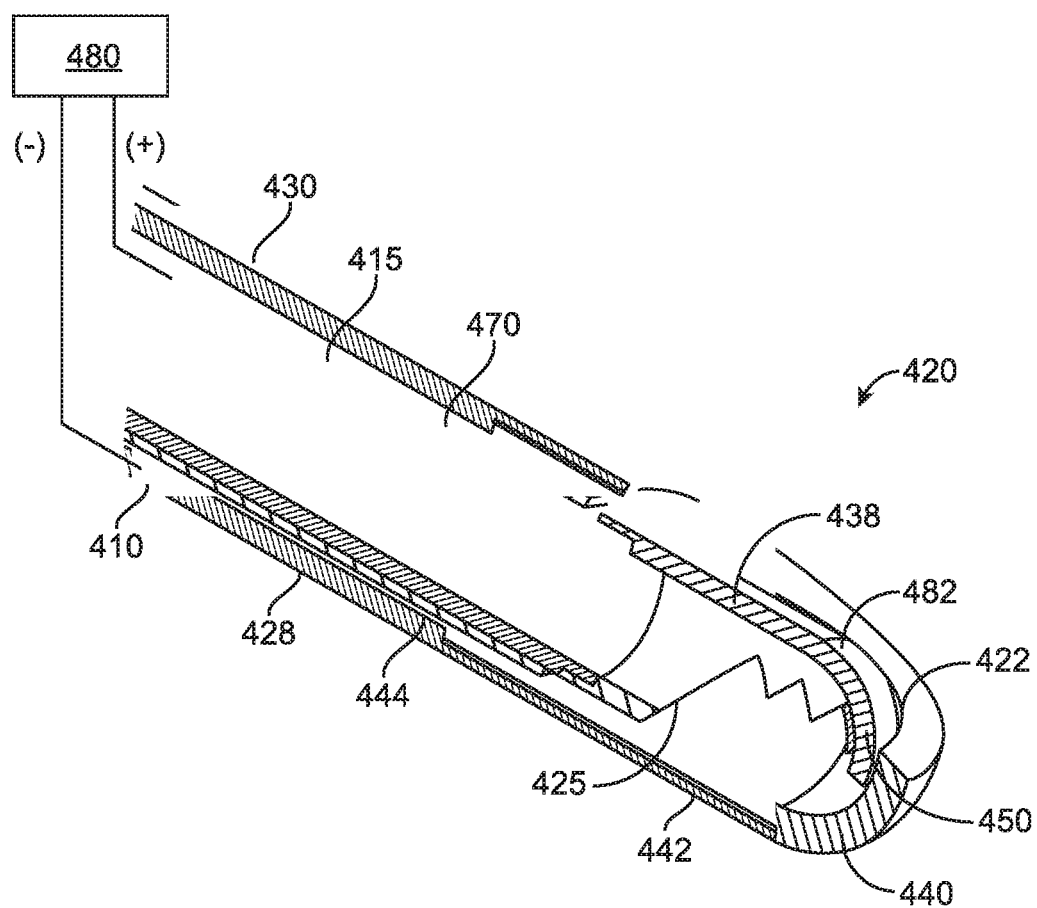
FIG. 13 is a sectional view of the working end of FIG. 10 taken along line 13-13 of FIG. 10.

FIG. 13 is a longitudinal sectional view of the working end 420 of the probe of FIGS. 10-11C which shows the working end 420 window-closed position. It can be seen that the working end 438 of the inner sleeve 415 is in close tolerance with bore 444 in outer sleeve and dielectric housing 440 so that rotation of inner sleeve 415 can shear tissue engaged by the inner sleeve and outer sleeve windows 422, 425. FIG. 13 further illustrates the support portion 442 of the metal outer sleeve 428 that extends underneath the ceramic housing 440. In addition, FIG. 13 also shows the thin insulating layer 470 that surrounds the inner sleeve 415 to electrically insulate the inner sleeve from the metal outer sleeve 428.

Still referring to FIG. 13, an RF source 480 is coupled to both the inner sleeve 410 and the outer sleeve 415 to provide for electrosurgical functionality. The RF source 480 is capable of delivering an average of at least 100 W, or at least 200 W, or at least 300 W or at least 400 W to allow for ignition of a plasma over the exposed outward or exterior surface 482 of the inner sleeve 415 in the window-closed position as shown in FIG. 10. Typically, the outward surface 482 of the inner sleeve 415 in the window-closed position is less than 15 mm$^2$, less than 10 mm$^2$ or less than 8 mm$^2$. In operation, it can be thus understood that rotation of the inner sleeve 415 in the outer sleeve 410 in a first mode of operation can mechanically shear tissue engaged by the windows 422 and 425 or in a second mode of operation to electrosurgically resect tissue. That is, the inner sleeve can rotate and shear tissue contemporaneously the RF source 480 delivers the cutting current to the inner sleeve to energize the edges of the inner sleeve window 425 which can create a plasma to shear tissue, or to assist in shearing tissue.

In general, a resecting probe or treatment device corresponding to the invention comprises shaft assembly 405 having an outer sleeve 410 and a rotatable inner sleeve 415 co-axially received in a bore 444 in outer sleeve, wherein the inner and outer sleeves have respective inner and outer cutting windows, 422 and 425, with cooperating cutting edges in distal portions thereof, and wherein the distal portion of the outer sleeve that carries the cutting window 422 comprises a dielectric housing 440 and the distal working end 438 of the inner sleeve 415 that carries the inner cutting window 425 comprises an RF electrode 450.

In this variation, the dielectric material of the dielectric housing can comprises at least one of a ceramic, a glass and a polymer. For example, the ceramic material can be selected from the group consisting of alumina, zirconia, silicon nitride, yttria-stabilized zirconia, magnesia-stabilized zirconia, ceria-stabilized zirconia and zirconia toughened alumina.

The probe of FIG. 10 further comprises a motor configured to selectively rotate in the inner sleeve in first and second rotational directions, with the radiofrequency (RF) source 480 coupled to the electrode. Further, a controller is operatively coupled to the motor and to the RF source.

In general, the controller includes an algorithm for stopping the motor to position the inner sleeve in a window-closed position or a window-open position. Further, the controller is configured to selectively operate in (i) a first mode in which the motor rotates or oscillates the inner sleeve with the RF electrode not energized for mechanically cutting tissue; (ii) a second mode in which the motor rotates or oscillates the inner sleeve with the RF electrode energized for electrosurgically cutting tissue; (iii) a third mode in which the inner sleeve is stationary in the window-closed position and the RF electrode is energized for applying coagulative or ablative energy to tissue; and (iv) a fourth mode in which the inner sleeve is stationary in the window-open position and the RF electrode is energized for applying coagulative or ablative energy to tissue.

Figure 14:
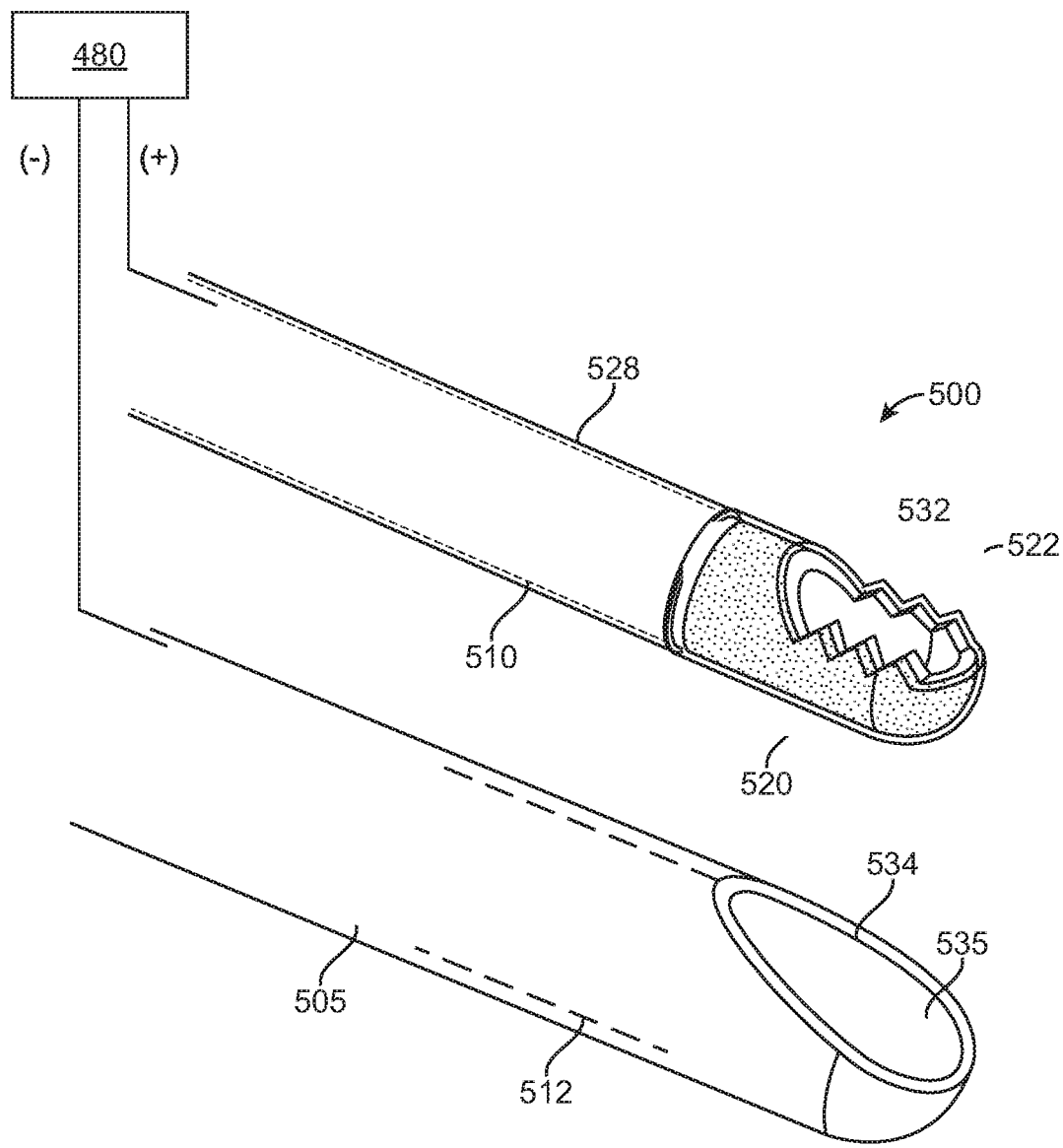
FIG. 14 illustrates another variation of a working end that includes an outer sleeve and inner sleeve.

FIG. 14 illustrates another variation of a working end 500 that includes an outer sleeve 505 and inner sleeve 510 that is adapted to rotate in bore 512 of the outer sleeve. In this variation, the outer sleeve 505 comprises a conductive metal tube without the ceramic housing as in the previous variation of FIGS. 10 and 11A. In this variation, the dielectric component that separates the conductive inner sleeve 510 from the conductive outer sleeve comprises a dielectric coating or layer 520 on the distal end 522 of the inner sleeve 510 and the polymer coating 528 over the proximal and medial portions of the inner sleeve 510. The dielectric material 520 at the distal end 522 of the inner sleeve can be a ceramic or a glass material that can be configured with sharp edges 532 so as to provide a sharp, durable cutting edge 532 for cooperating with the edges 534 of the outer sleeve window 535. In all other respects, the variation of FIG. 14 can operate is the same manner as the variation described above in FIGS. 10-13.

Figure 15:
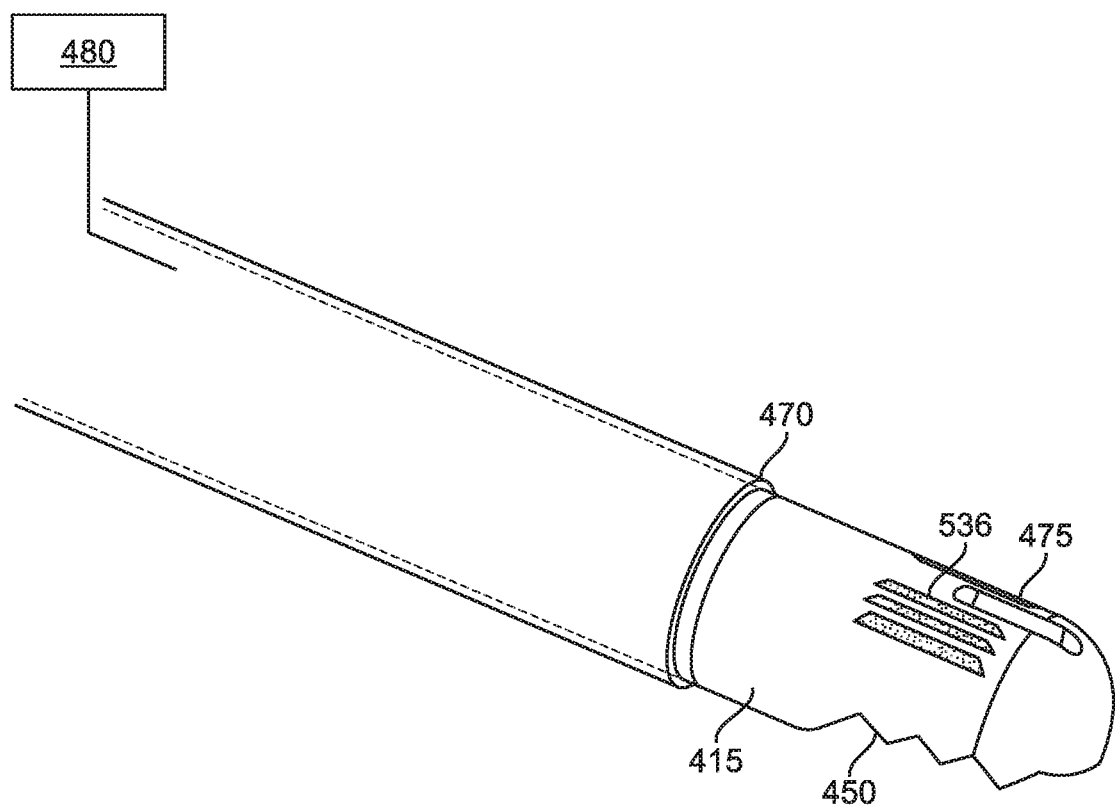
FIG. 15 is a perspective view of a working end of a motor-driven, rotating inner sleeve similar to that of FIGS. 11B-11C with abrasive cutting features for abrading bone.

FIG. 15 is a perspective view of a working end of a motor-driven, rotating inner sleeve similar to that of FIGS. 11B-11C with abrasive cutting features or sharp edges 536 for abrading bone. Thus, another mode of operation can be to rotate the inner sleeve at high speeds to use the abrasive features 536 to cut or abrade bone, typically without RF current being applied to the electrode surface. In some methods, and RF current can be applied to the electrode surface while abrading hard tissue or cauterizing purposes.

Figure 16:
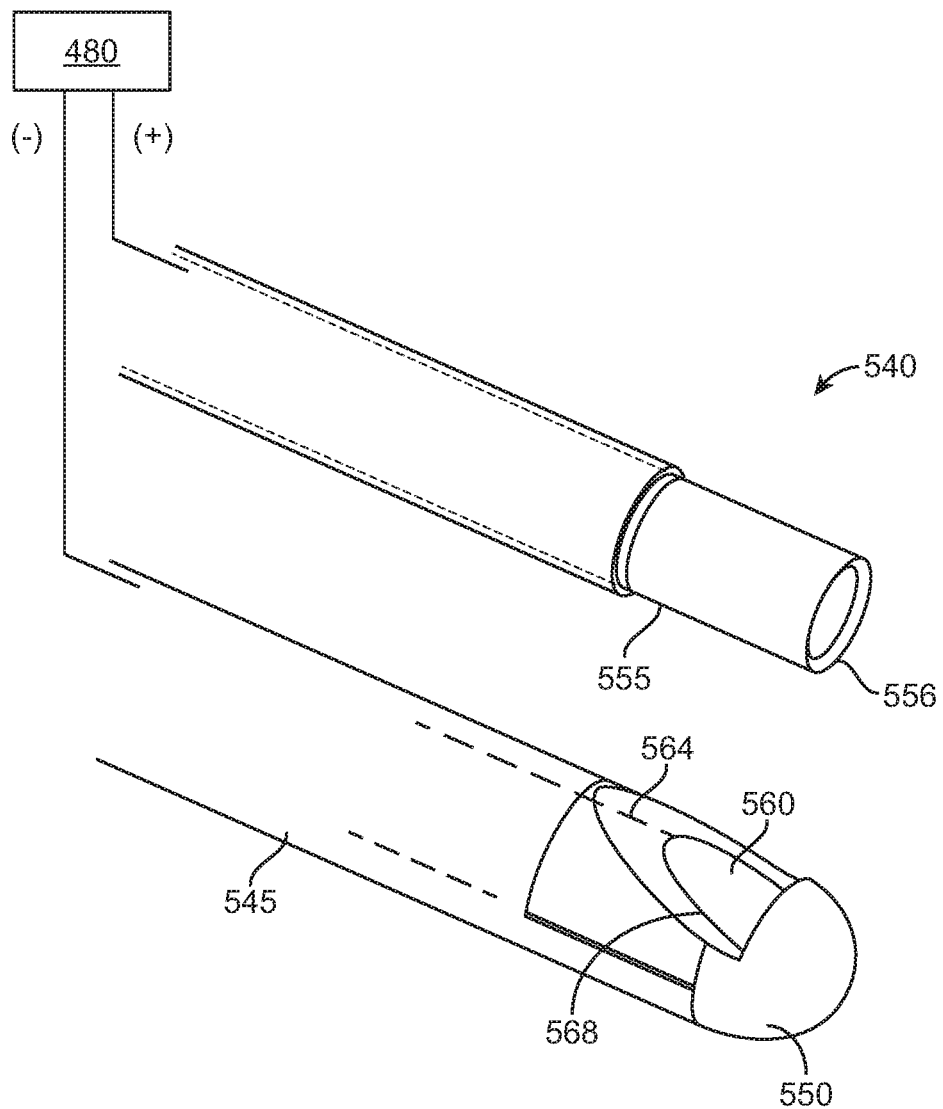
FIG. 16 is a perspective view of a working end of another variation of a probe that shows a motor-driven, reciprocating inner sleeve comprising an electrode that reciprocates in a dielectric housing carried by the outer sleeve.

FIG. 16 illustrates another variation of working end 540 that operates under similar principles to that of the variation of FIG. 10 wherein the outer sleeve 545 carries a distal dielectric or ceramic housing 550 and a concentric inner sleeve 555 with cutting edges 556 is adapted to move relative to the outer sleeve window 560 in the dielectric housing 550. However, in this variation, the inner sleeve 555 is adapted to reciprocate rather than rotate. In other respects, the cutting edges 556 of the inner sleeve 555 are configured with a close fit to the bore 564 in the dielectric housing 550 such that the inner sleeve cutting edges 556 and the edges 568 of outer sleeve window 560 shear tissue engaged by the window 560. As described in previous embodiments, an RF source 480 is operatively coupled to both the inner and outer sleeves 545 and 555 to allow for electrosurgical cutting. In use, the reciprocation of inner sleeve thus can resect tissue mechanically or electrosurgically as described above.

Figure 17:
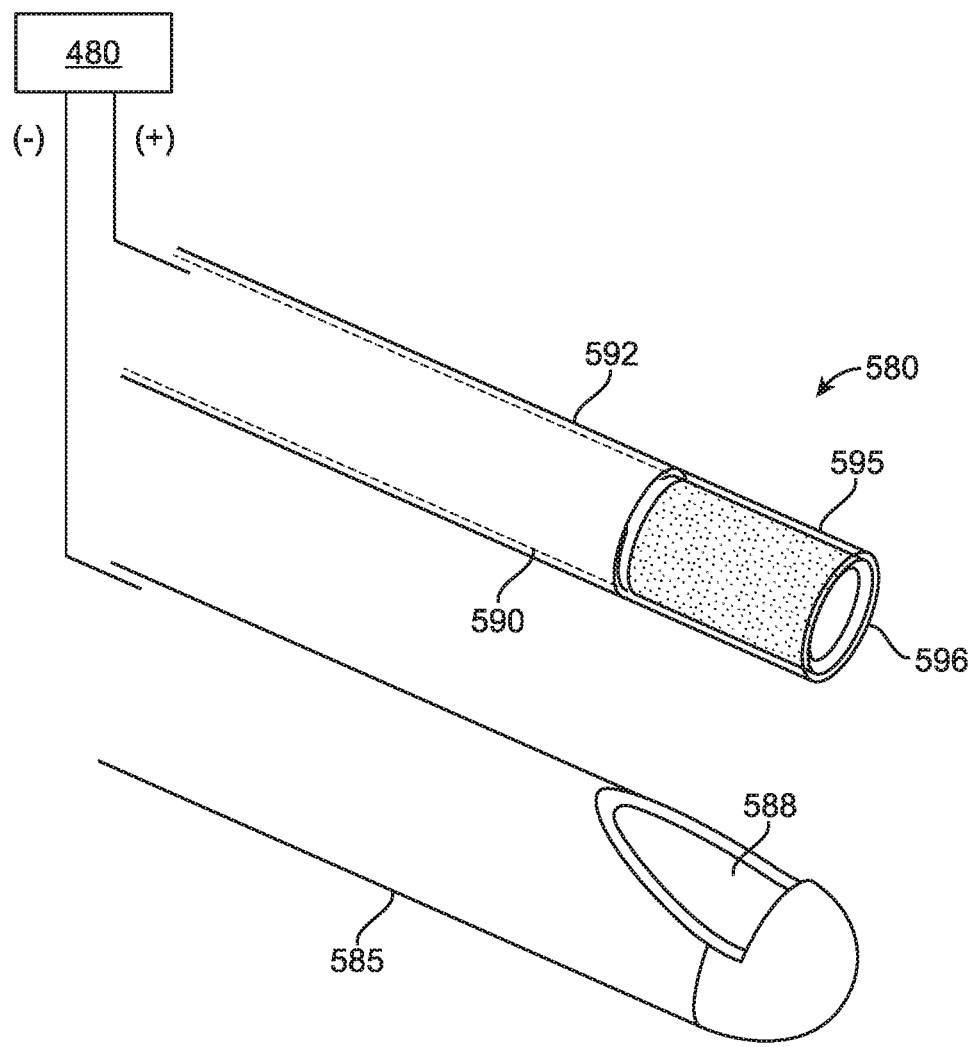
FIG. 17 is a perspective view of a working end of another variation of a probe that shows a reciprocating inner sleeve with a ceramic or glass cutting edge surrounding an electrode sleeve that reciprocates in a metal outer sleeve.

FIG. 17 illustrates another variation of working end 580 that again is similar to that of FIGS. 14 and 15. In this variation, the outer sleeve 585 comprises a thin wall conductive metal with window 588 therein. The inner sleeve 590 comprises a metal sleeve encased in an insulative polymer 592 and a distal ceramic or glass portion 595 that functions as an electrical insulator as well as providing a cutting edge 596. In this variation, the inner sleeve 590 again is adapted to reciprocate rather than rotate in the outer sleeve window 588. Again, an RF source 480 is operatively coupled to both the inner and outer sleeves 585 and 590 to allow for electrosurgical cutting. In use, the reciprocation of inner sleeve and thus can resect tissue mechanically or electrosurgically as described above.

Figure 18:
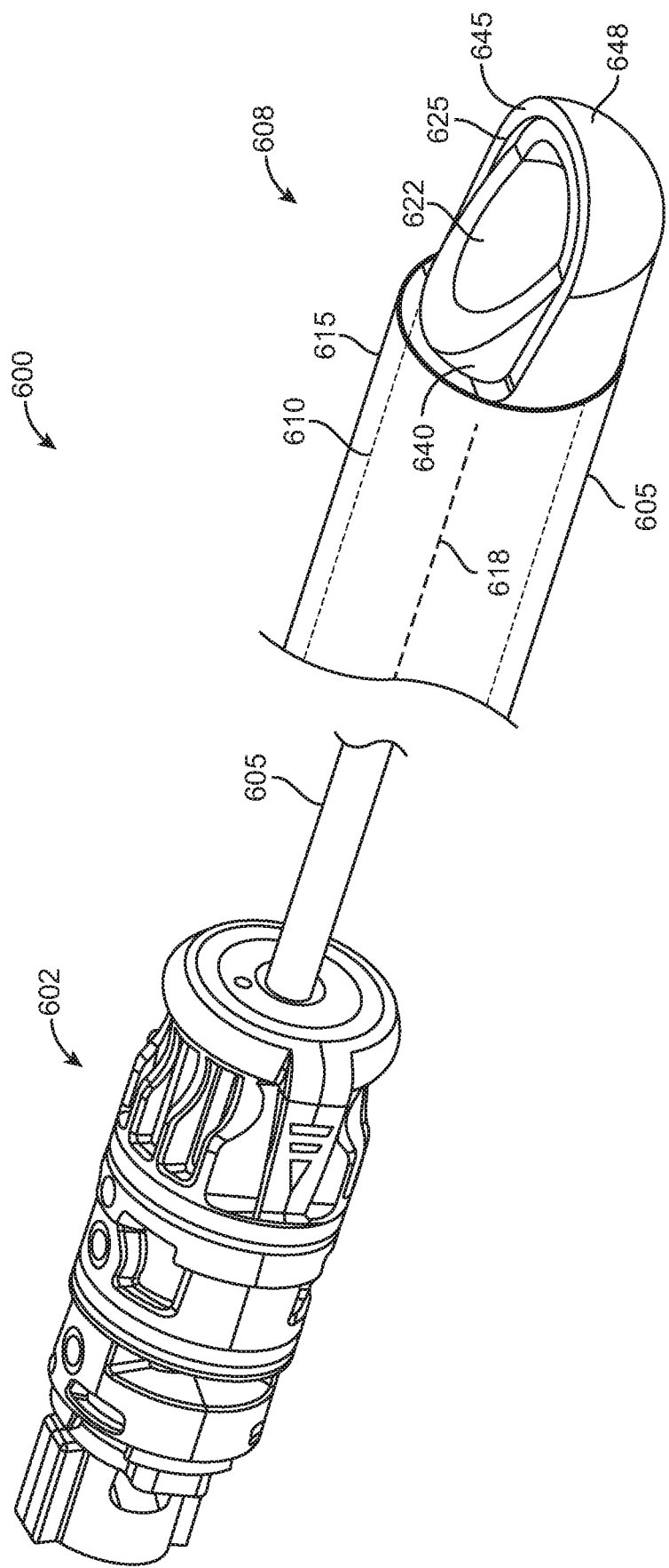
FIG. 18 is a perspective view of another variation or a probe that has a rotating inner sleeve that carries a windowed ceramic cutter that rotates in a concentric windowed metal outer sleeve wherein the edges of the outer sleeve window comprise an active electrode wherein the probe allows for both mechanical and electrosurgical cutting.
Figure 19:
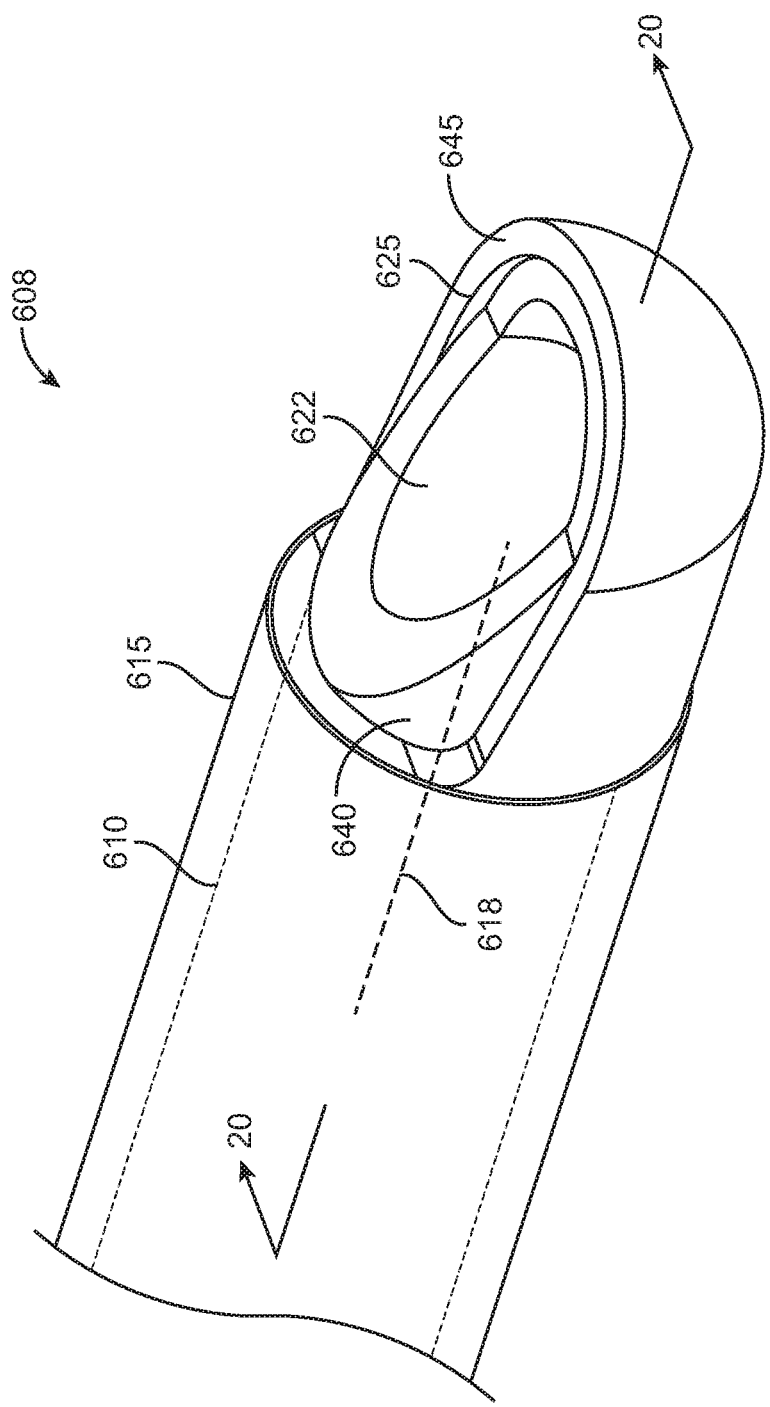
FIG. 19 is an enlarged view of the working end of FIG. 18.
Figure 20:
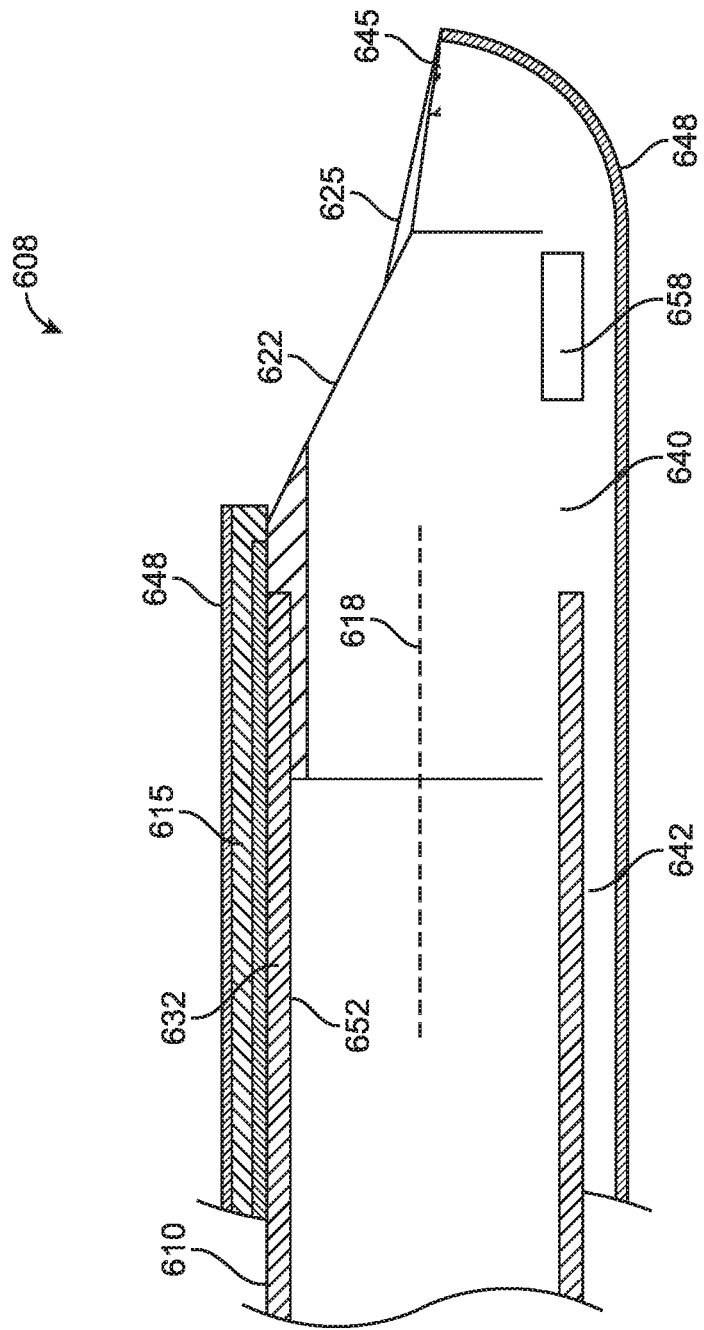
FIG. 20 is a longitudinal sectional view of the working end of FIG. 19 taken along line 20-20 of FIG. 19 showing the active and return electrodes.

Now turning to FIGS. 18-20, another variation of an arthroscopic shaver or resection probe is shown which somewhat similar to that of FIGS. 1 and 3A-3B and comprises a tubular cutter 600 having a proximal hub 602 coupled to an elongated shaft assembly 605 having a distal working end 608 as shown in FIG. 18. The shaft assembly 605 comprises a first or inner sleeve 610 (FIG. 19, shown in broken line) and a second, concentric outer sleeve 615, with both sleeves located coaxially over a longitudinal axis 618. The working end 608 has a first or inner sleeve window 622 that cooperates with a second or outer sleeve window 625 for engaging and resecting tissue.

The proximal hub 602 may be of the type shown in FIG. 10 and will be adapted for coupling to a hand piece and motor drive operated by a controller. The controller will programmed with algorithms, as described in previous embodiments, for rotating the inner sleeve 610 relative to the outer sleeve 615 as well as for stopping the inner sleeve 610 in a selected rotational position, such as a window-closed position (where inner and outer windows 622 and 625 are out of alignment) or a window-open position (where inner and outer windows 622 and 625 are aligned).

In the variation in FIGS. 18 and 19, the shaft assembly 605 differs from previous embodiments in that the inner sleeve 610 has a proximal portion comprising a thin-wall tubular conductive member 632 (FIG. 20) that carries a distal, dielectric cutter member 640 that is formed of a dielectric material, such as a ceramic (see FIGS. 19 and 20). Thus, the inner sleeve window 622 is formed through a wall of the dielectric cutter 640. The outer sleeve 615 is typically a thin-wall conductive metal tube, and the outer window 625 is typically formed through a wall of the outer sleeve.

An insulator layer or sleeve 642 is provided between the inner sleeve 610 and the outer sleeve 615 which overlaps the dielectric cutter 640 to thus electrically insulate the sleeves 610 and 615 from one another. Further, except for exposed edges 645 of the outer sleeve window 625, the outer sleeve 615 is covered with a dielectric coating 648. The insulator layer 648 can comprise a ceramic material, a glass material, a polymeric material or a combination thereof. The layer 648 also can comprise a mating sleeve of a ceramic or glass that is formed with a tight fit around the distal end and window 625 of the outer sleeve 615. The term tight fit means that the gap between any such ceramic or glass sleeve in the metal outer sleeve 625 is less than 0.010" or more often less than 0.005" to prevent plasma migration into such a gap. Thus, the window edges 645 are adapted to function as an active electrode while the remainder of the outer sleeve surface is insulated. In one variation, an inner surface 652 of the thin wall conductive member 632 comprises a return electrode (see FIG. 20).

In another variation, a return electrode can be positioned on an exterior surface of the outer dielectric coating or layer 648 spaced proximally from the window 625 in the out sleeve 615. It should be appreciated that the embodiment described above is configured for maintaining a cutting plasma about the window edge 645 wherein power is delivered from an RF source in a range of 100 W to 400 W typically. When plasma is generated about the window edge 645 and such power levels, the plasma is highly energetic and can degrade or disintegrate many insulator materials. For this reason, the use of glass and ceramic layers are described and preferred. In another mode of operation, lower levels of power from an RF source can be used for simple coagulation of tissue, for example 10 W to 50 W. However, at such low power levels, insulator layers can be much less robust and can comprise polymeric layers or coatings.

Referring to FIG. 20, it can be seen that the working end of the dielectric cutter 640 has at least one aperture or window 658 opposing the larger cutting window 622. Such an aperture or window 658 is sized and adapted to allow saline flow through the probe continuously when the inner sleeve window 622 is out of alignment with the outer sleeve window 625.

In one variation, the dielectric cutting member 640 has a first window that has an area of at least 50% of the area of the tissue-receiving window 625 of the outer sleeve 615 and a second aperture or window 658 with area of less 25% of said tissue-receiving window 625 of the outer sleeve 615.

Thus, the probe can be used in a first mode of operation in which the inner sleeve 610 and distal dielectric cutter 640 rotates in the outer sleeve 615 to cut tissue mechanically without the application of RF current.

In a second mode of operation, both the inner sleeve 610 and dielectric cutter 640 can rotate and the RF source can be activated to form plasma about the electrically conductive edges 645 surrounding the outer window 625 which act as an active electrode. RF can be delivered to the outer sleeve 615 while the conductive surface 652 of the lumen of the inner sleeve 610 can act as the return electrode to provide such electrosurgical tissue cutting or resection.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. An arthroscopic cutting probe, comprising:
a proximal hub;
an elongated shaft assembly that extends distally from the proximal hub to a working end of the arthroscopic cutting probe, the elongated shaft assembly comprising an outer metal sleeve and an inner metal sleeve that is rotationally disposed in a longitudinal bore of the outer metal sleeve, wherein the outer metal sleeve is electrically couplable to an RF source and includes an exterior, the outer metal sleeve further including an outer cutting window and exposed window edges surrounding the outer cutting window at the working end of the arthroscopic cutting probe, wherein, at the working end of the arthroscopic cutting probe, said outer metal sleeve is electrically insulated over the exterior of the outer metal sleeve while leaving the exposed window edges uninsulated and functioning as an active electrode in the arthroscopic cutting probe when the outer metal sleeve is electrically coupled to the RF source, the exposed window edges functioning as the only active electrode at the working end of the arthroscopic cutting probe, the exposed window edges comprising sharp edges for cutting tissue, wherein the inner metal sleeve is electrically couplable to the RF source and includes an exterior, a distal end, a proximal end and a longitudinal passageway therein, and wherein, at the working end of the arthroscopic cutting probe, said inner metal sleeve is electrically insulated over the exterior of the inner metal sleeve while maintaining an electrically conductive inner surface that functions as a return electrode in the arthroscopic cutting probe when the inner metal sleeve is electrically coupled to the RF source, wherein, when the inner metal sleeve is electrically coupled to the RF source, the electrically conductive inner surface maintained by the inner metal sleeve functions as the only return electrode at the working end of the arthroscopic cutting probe; and
a dielectric cutting member attached to the distal end of the inner metal sleeve, wherein said dielectric cutting member has a distal end, a proximal end and a central passage therein, the central passage extending from an inner cutting window in the dielectric cutting member at the distal end of the dielectric cutting member to an opening at the proximal end of the dielectric cutting member, wherein the opening at the proximal end of the dielectric cutting member is contiguous with the longitudinal passageway in the inner metal sleeve,
wherein the inner metal sleeve is rotatable relative to the outer metal sleeve to cause the inner cutting window to rotate past the outer cutting window to resect tissue received in the inner cutting window through the outer cutting window while the exposed window edges remain stationary relative to the rotating inner metal sleeve.

2. The arthroscopic cutting probe of claim 1, wherein the proximal end of the dielectric cutting member is received in the distal end of the inner metal sleeve.

3. The arthroscopic cutting probe of claim 1, wherein the entirety of the dielectric cutting member is formed with a dielectric material.

4. The arthroscopic cutting probe claim 3, wherein the dielectric material comprises a wear-resistant ceramic material selected from the group consisting of yttria-stabilized zirconia, magnesia-stabilized zirconia, ceria-stabilized zirconia, zirconia toughened alumina and silicon nitride.

5. The arthroscopic cutting probe of claim 1, wherein the outer metal sleeve is bullet-shaped at the working end of the arthroscopic cutting probe with the outer cutting window formed thereacross.

6. The arthroscopic cutting probe of claim 5, wherein the distal end of the dielectric cutting member is bullet-shaped with the inner cutting window formed thereacross.

7. The arthroscopic cutting probe of claim 6, wherein the inner cutting window can be aligned with the outer cutting window to nest in the outer cutting window.

8. The arthroscopic cutting probe of claim 2, wherein an insulating layer received on the exterior of the inner metal sleeve partially overlaps onto an outer surface of the dielectric cutting member at the proximal end of the dielectric cutting member.

9. The arthroscopic cutting probe of claim 1, wherein the dielectric cutting member has an aperture disposed in a wall of the dielectric cutting member at a location opposite to the inner cutting window.

10. The arthroscopic cutting probe of claim 9, wherein the inner cutting window has an area of at least 50% of an area of the outer cutting window.

11. The arthroscopic cutting probe of claim 10, wherein the aperture has an area of less than 25% of the outer cutting window.

12. An arthroscopic cutting system, said cutting system comprising:
- an arthroscopic cutting probe as in claim 1;
- a motor drive unit configured to be coupled to the inner metal sleeve to rotate the inner metal sleeve relative to the outer metal sleeve;
- a radiofrequency (RF) power supply configured to be coupled to the active electrode and the return electrode; and
- a controller configured to control the motor drive unit and the RF power supply.

13. The arthroscopic cutting system of claim 12, wherein the controller is configured to operate the motor drive and RF power supply in a first mode for mechanical tissue cutting in which the motor drive is activated and the RF power supply is not activated and a second mode for a combination of mechanical and electrosurgical tissue cutting in which the motor drive is activated and the RF power supply is activated.

14. The arthroscopic cutting system of claim 12 further comprising a negative pressure source configured to be coupled to the longitudinal passageway in the inner metal sleeve to draw tissue through the outer cutting window and the inner cutting window.

15. The arthroscopic cutting probe of claim 14, wherein the controller is configured to operate the negative pressure source.

16. A method for resecting tissue, said method comprising:
- providing an arthroscopic cutting probe as in claim 1;
- engaging the dielectric cutting member against tissue;
- rotating the inner cutting window past the outer cutting window.

17. The method of claim 16, wherein the inner cutting window is rotated during at least some time periods without applying RF current to the active electrode in a first mechanical resection mode of operation.

18. The arthroscopic cutting probe of claim 1, wherein the inner metal sleeve is rotatable relative to the outer metal sleeve between a first position in which the inner cutting window is open and a second position in which the inner cutting window is closed.

19. The arthroscopic cutting probe of claim 18, wherein, when the inner cutting window is closed, the active electrode is closed off from the return electrode.

\* \* \* \* \*